United States Patent
Long et al.

(10) Patent No.: US 11,452,640 B2
(45) Date of Patent: Sep. 27, 2022

(54) DRESSING WITH BOLSTER FOR LINEAR TISSUE SITES

(71) Applicant: KCI Licensing, Inc., San Antonio, TX (US)

(72) Inventors: Justin Alexander Long, Bournemouth (GB); Timothy Mark Robinson, Shillingstone (GB); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 529 days.

(21) Appl. No.: 16/254,340

(22) Filed: Jan. 22, 2019

(65) Prior Publication Data

US 2019/0262181 A1    Aug. 29, 2019

Related U.S. Application Data

(60) Provisional application No. 62/634,566, filed on Feb. 23, 2018.

(51) Int. Cl.
*A61F 13/00* (2006.01)
*A61F 13/02* (2006.01)
(Continued)

(52) U.S. Cl.
CPC .... *A61F 13/00068* (2013.01); *A61F 13/0216* (2013.01); *A61M 1/0023* (2013.01);
(Continued)

(58) Field of Classification Search
CPC ............ A61F 13/00068; A61F 13/0216; A61F 2013/00174; A61M 1/0023; A61M 1/0088; A61M 27/00
See application file for complete search history.

(56) References Cited

U.S. PATENT DOCUMENTS 1,355,846 A    10/1920    Rannells
2,547,758 A    4/1951    Keeling
(Continued)

FOREIGN PATENT DOCUMENTS

AU    550575 B2    3/1986
AU    745271 B2    3/2002
(Continued)

OTHER PUBLICATIONS

European International Search Report and Written Opinion for Corresponding Application No. PCT/US2019/014612, dated Apr. 8, 2019.
(Continued)

*Primary Examiner* — Tatyana Zalukaeva
*Assistant Examiner* — Nhu Q. Tran

(57) ABSTRACT

Dressings for closing an opening through a surface of a tissue site are described. The dressing includes a cover adapted to form a sealed space over the opening and a bolster. The bolster is adapted to be positioned adjacent the opening and includes a first plurality of holes. The holes have an average width to length ratio causing the plurality of holes to collapse in a direction substantially perpendicular to the opening. Systems, apparatuses, kits and methods including and/or using the dressing for closing the opening are also described.

23 Claims, 14 Drawing Sheets

(51) Int. Cl.
    *A61M 1/00*     (2006.01)
    *A61M 27/00*     (2006.01)

(52) U.S. Cl.
    CPC ..... *A61M 1/90* (2021.05); *A61F 2013/00174* (2013.01); *A61M 27/00* (2013.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,846,141 B2 | 12/2010 | Weston | |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2009/0299307 A1* | 12/2009 | Barta | A61F 13/00038 604/319 |
| 2014/0163491 A1 | 6/2014 | Schuessler et al. | |
| 2015/0080788 A1 | 3/2015 | Blott et al. | |
| 2015/0320434 A1* | 11/2015 | Ingram | A61B 17/22004 606/131 |
| 2015/0320602 A1 | 11/2015 | Locke et al. | |
| 2015/0320603 A1 | 11/2015 | Locke et al. | |
| 2016/0144084 A1* | 5/2016 | Collinson | A61F 13/00068 604/319 |
| 2017/0143552 A1* | 5/2017 | Hartwell | A61F 13/0233 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |

(56) References Cited

FOREIGN PATENT DOCUMENTS

| | | |
|---|---|---|
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 2009066106 A1 | 5/2009 |
| WO | 2015193257 A1 | 12/2015 |
| WO | 2017040045 A1 | 3/2017 |
| WO | 2018226669 A1 | 12/2018 |
| WO | 2018226705 | 12/2018 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31,1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

(56) References Cited

OTHER PUBLICATIONS

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

\* cited by examiner

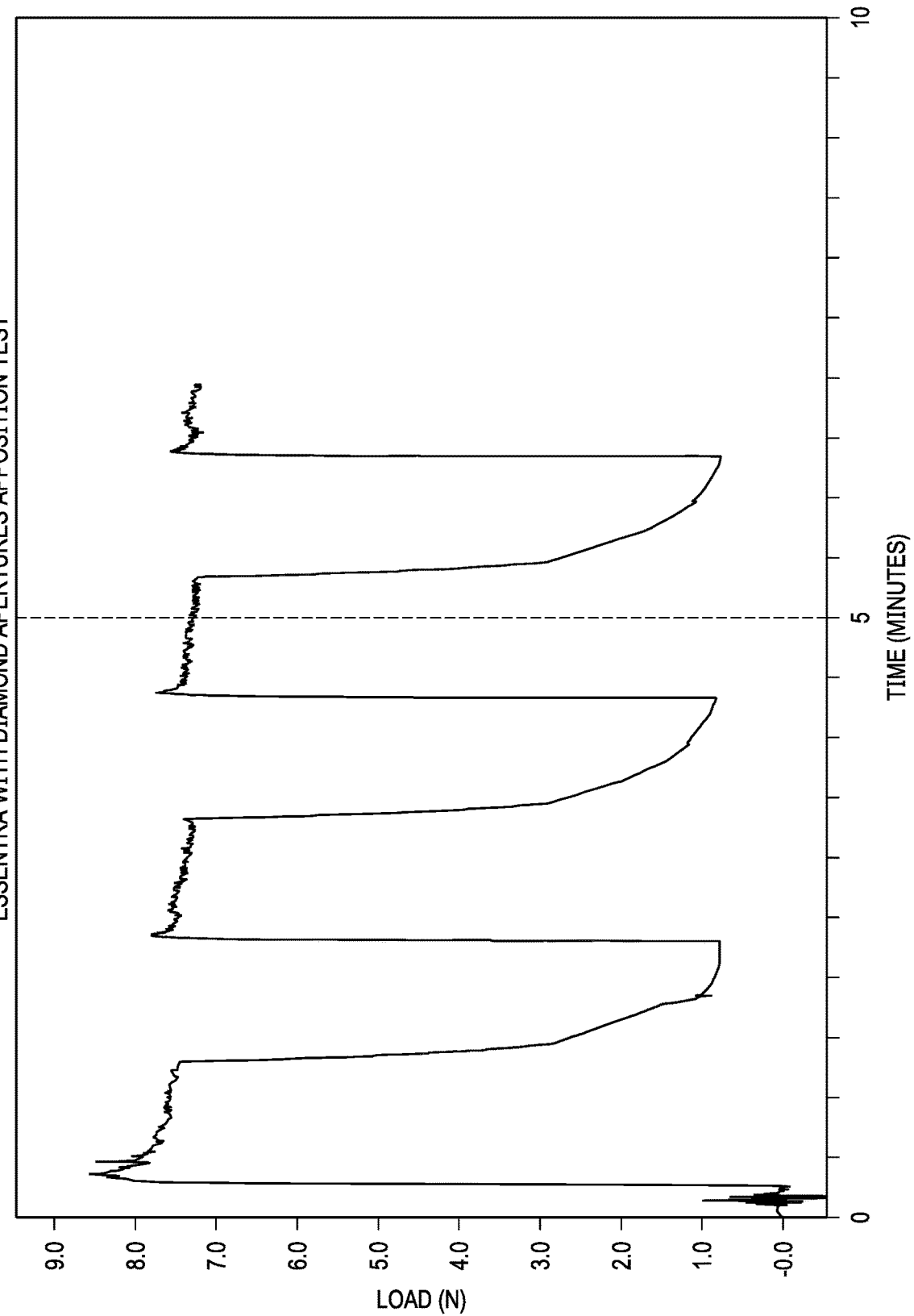

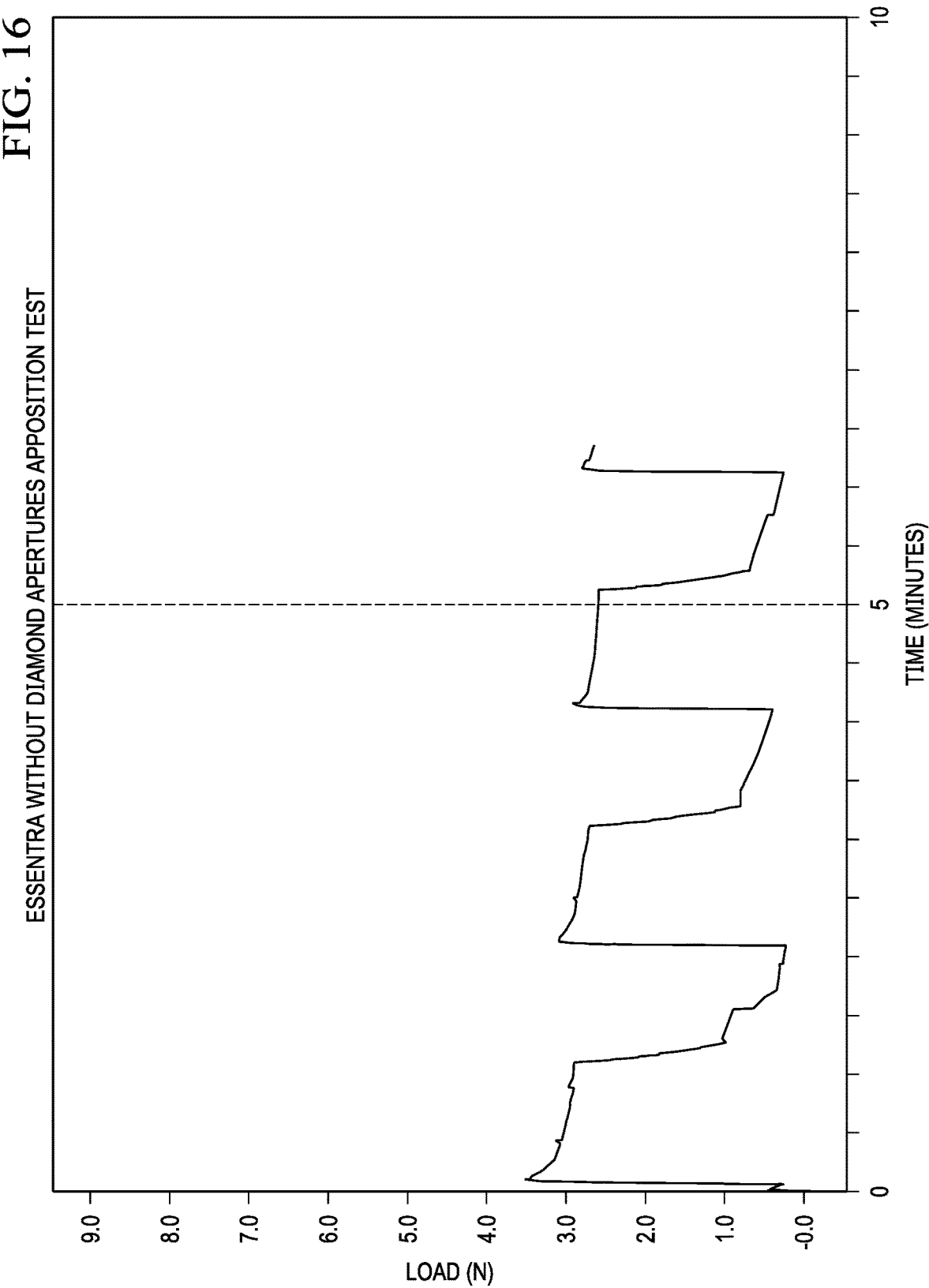

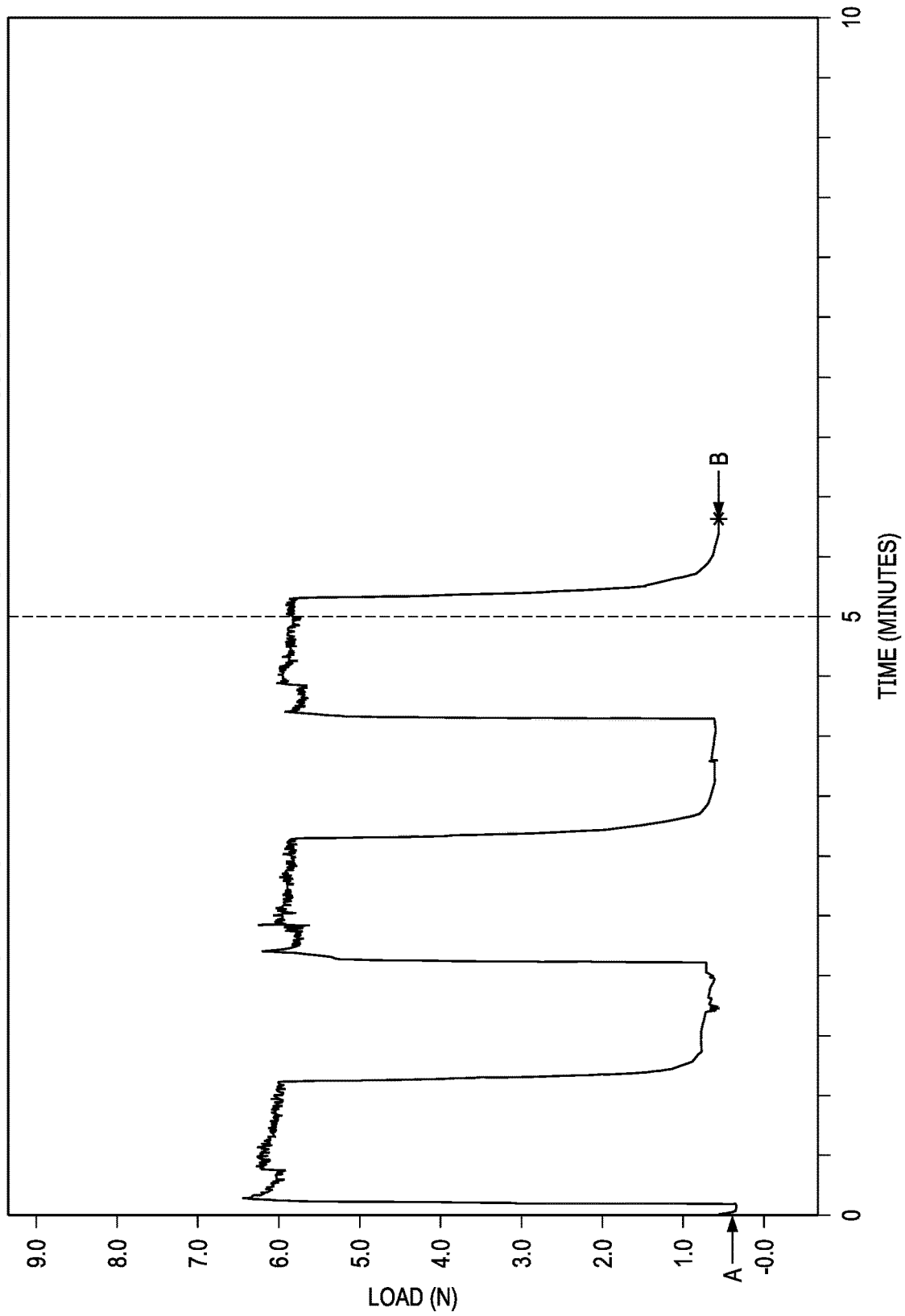

DRESSING WITH BOLSTER FOR LINEAR TISSUE SITES

RELATED APPLICATIONS

The present invention claims the benefit under 35 U.S.C. § 119(e), of the filing of U.S. Provisional Patent Application Ser. No. 62/634,566, filed Feb. 23, 2018, the disclosure of which is hereby incorporated by reference in its entirety.

TECHNICAL FIELD

The invention set forth in the appended claims relates generally to dressings, systems, apparatuses, kits and methods for treating a tissue site and more particularly, but without limitation, to a dressing having a bolster for assisting in closure of linear wounds.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, improvements to therapy systems, components, and processes may benefit healthcare providers and patients.

BRIEF SUMMARY

New and useful dressing, systems, apparatuses, kits and methods for closing an opening through a surface of a tissue site are set forth in the appended claims. Illustrative embodiments are also provided to enable a person skilled in the art to make and use the claimed subject matter.

For example, a dressing for closing an opening through a surface of a tissue site is described. The dressing may include a cover adapted to form a sealed space over the opening and a bolster. The bolster can have a first surface and a second surface and be adapted to be positioned adjacent to the opening. The bolster can further include a first plurality of holes extending through at least a portion of the bolster. The holes may have an average width to length ratio ≤about 0.50.

An alternative dressing for closing an opening through a surface of a tissue site is also described. The dressing may include a cover adapted to form a sealed space over the opening and a bolster. The bolster can have a first surface and a second surface and be adapted to be positioned adjacent to the opening. The bolster can further include a first plurality of holes extending through at least a portion of the bolster. The holes can have an average width to length ratio about 0.050 to about 0.50. The bolster may have a thickness of about 1.0 mm to about 6.0 mm, and the bolster may include a non-woven material or a compressed foam.

Alternatively, other example embodiments may include a system for closing an opening through a surface of a tissue site. The system may include the dressing and a negative-pressure source adapted to be fluidly coupled to the dressing. The dressing may include a cover adapted to form a sealed space over the opening and a bolster. The bolster can have a first surface and a second surface and be adapted to be positioned adjacent to the opening. The bolster can further include a first plurality of holes extending through at least a portion of the bolster. The holes may have an average width to length ratio ≤about 0.50.

A method for treating a tissue site on a patient is also described. The method may include positioning a dressing comprising a bolster adjacent to the tissue site. The bolster can have a first surface and a second surface. The bolster can further include a first plurality of holes extending through at least a portion of the bolster. The holes may have an average width to length ratio ≤about 0.50. The method may further include collapsing the bolster parallel to the surface of the tissue site to generate a closing force on the tissue site.

A dressing kit is also described. The dressing kit may include a bolster and optionally, one or more of a cover, a protective layer and a top layer. The bolster can include a first surface, a second surface, and a first plurality of holes extending through at least a portion of the bolster. The holes can have an average width to length ratio ≤about 0.50. The bolster may have a thickness of ≤about 6.0 mm. The cover may be separate from the bolster or adjacent to the first surface of the bolster. The protective layer may include a second plurality of holes extending through at least a portion of the protective layer. The protective layer may be separate from the bolster or adjacent to the second surface of the bolster, and the second plurality of holes may be substantially adjacent to the first plurality of holes. The top layer may be separate from the bolster or adjacent to the first surface of the bolster.

Objectives, advantages, and a preferred mode of making and using the claimed subject matter may be understood best by reference to the accompanying drawings in conjunction with the following detailed description of illustrative embodiments.

BRIEF DESCRIPTION OF THE DRAWINGS

FIG. 15 illustrates results of apposition testing of Essentra bolster with diamond shaped holes.

FIG. 16 illustrates results of apposition testing of Essentra bolster without diamond shaped holes.

FIG. 17 illustrates results of apposition testing of silicone polymeric ball and strut bolster with diamond shaped holes.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

I. Dressing

Figure 1:
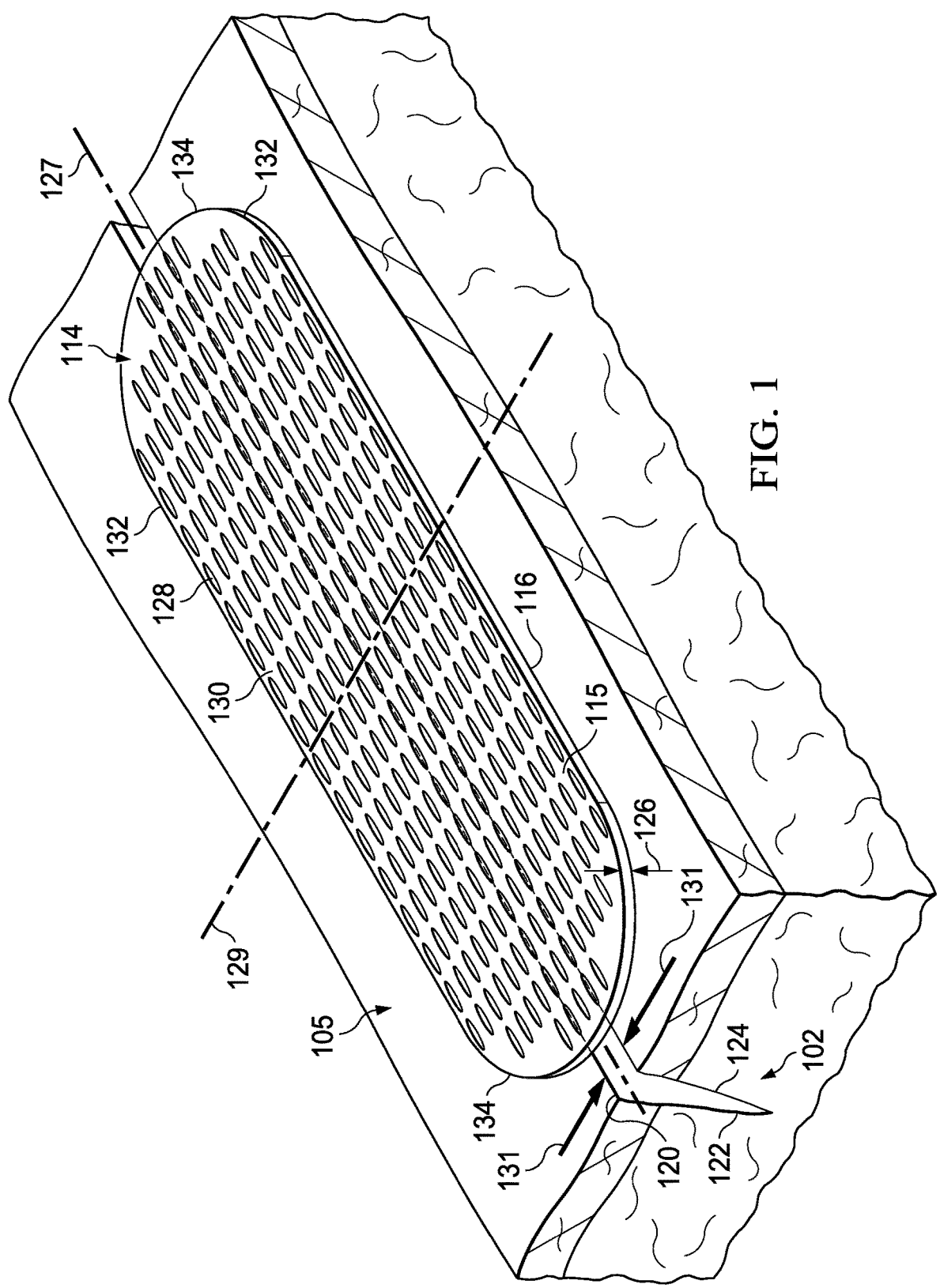
FIG. 1 is an isometric view, illustrating details that may be associated with some embodiments of a bolster for a dressing in a first position.

Dressings for closing an opening on a tissue site in a negative-pressure environment are described herein. A dressing may generally include a bolster. FIG. 1 illustrates details that may be associated with some embodiments of a bolster 114. In some embodiments, the bolster 114 may be a substantially flat or substantially planar body. The bolster 114 may have a first surface 115 (e.g., a back side) and second surface 116 (e.g., a tissue-facing side). In some embodiments, the bolster 114 may be adapted to be positioned adjacent to an opening 120 on a tissue site 102 so that the second surface 116 of the bolster 114 is in contact with a tissue surface surrounding the opening. As used herein, the term "tissue site" broadly refers to a wound or a defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be used at a tissue site to grow additional tissue that may be harvested and transplanted to a tissue site at another location.

A tissue site may also be characterized by shape. For example, some tissue sites may be referred to as a linear tissue site or a linear wound. A linear tissue site or linear wound may generally refer to a tissue site having an elongated shape, such as an incision having a length substantially greater than its width. An incision may have edges that may be substantially parallel, particularly if the incision is caused by a scalpel, knife, razor, or other sharp blade. Other examples of a linear tissue site or a linear wound may include a laceration, a puncture, or other separation of tissue, which may have been caused by trauma, surgery, or degeneration. In some embodiments, a linear tissue site or a linear wound may also be an incision in an organ adjacent a fistula. In some embodiments, a linear tissue site or a linear wound may be an incision or puncture in otherwise healthy tissue that extends up to 40 cm or more in length. In some embodiments, a linear tissue site or a linear wound may also vary in depth. For example, an incision may have a depth that extends up to 15 cm or more or may be subcutaneous depending on the type of tissue and the cause of the incision. In some embodiments, a linear tissue site or a linear wound may be present on an abdomen or a knee of a patient.

The bolster 114 may have a thickness 126. The thickness 126 may be any suitable thickness as needed for a tissue site. In some embodiments, the thickness 126 may be about 5 mm, about 10 mm or about 15 mm. Advantageously, in some embodiments, the bolster 114 may have a minimal thickness, for example, the thickness 126 may be ≤about 6 mm, ≤about 4 mm, ≤about 2 mm. In some embodiments, the thickness 126 may be about 1.0 mm to about 6.0 mm or about 2 mm to about 4.0 mm. In some embodiments, the bolster 114 may have a substantially uniform thickness 126. In other embodiments, the thickness may not be strictly uniform. In some embodiments, individual portions of the bolster 114 may have a minimal tolerance from the thickness 126. In some embodiments, the thickness 126 may have a tolerance of about 2 mm. The bolster 114 may be flexible so that the bolster 114 may be contoured to a surface of the tissue site 102.

In some embodiments, a bolster comprises a first plurality of holes or perforations extending through at least a portion of the bolster. For example, as shown in FIG. 1, the bolster 114 includes a first plurality of holes 128. In general, the holes 128 may extend substantially through the bolster 114, for example through the thickness 126 of the bolster 114. As illustrated in FIG. 1, for example, one or more of the holes 128 may be a through-hole that extends through the bolster 114 from the first surface 115 to the second surface 116.

In some embodiments, the first plurality of holes 128 may extend through the bolster 114 to form walls 130 extending through the bolster 114. In some embodiments, the walls 130 may be generally parallel to the thickness 126 of the bolster 114. In other embodiments, the walls 130 may be generally perpendicular to the surface of the bolster 114. In some embodiments, the holes 128 may have an elliptical shape as shown.

In some embodiments, the bolster 114 may have a first orientation line 127 and a second orientation line 129 that is perpendicular to the first orientation line 127. In some embodiments, an orientation line, such as the first orientation line 127 or the second orientation line 129, may be a line of symmetry of the bolster 114. A line of symmetry may be, for example, an imaginary line across a surface of the bolster 114 defining a fold line such that if the bolster 114 is folded on the line of symmetry, the holes 128 and the walls 130 would be coincidentally aligned.

Although the bolster 114 is shown as having a generally oblong shape including longitudinal edges 132 and latitudinal edges 134, the bolster 114 may have other shapes. For example, the bolster 114 may have a rectangular, diamond, square, or circular shape. In some embodiments, the shape of the bolster 114 may be selected to accommodate the type of tissue site being treated. In some embodiments, the first orientation line 127 may be parallel to the longitudinal edges 132.

Figure 2A:
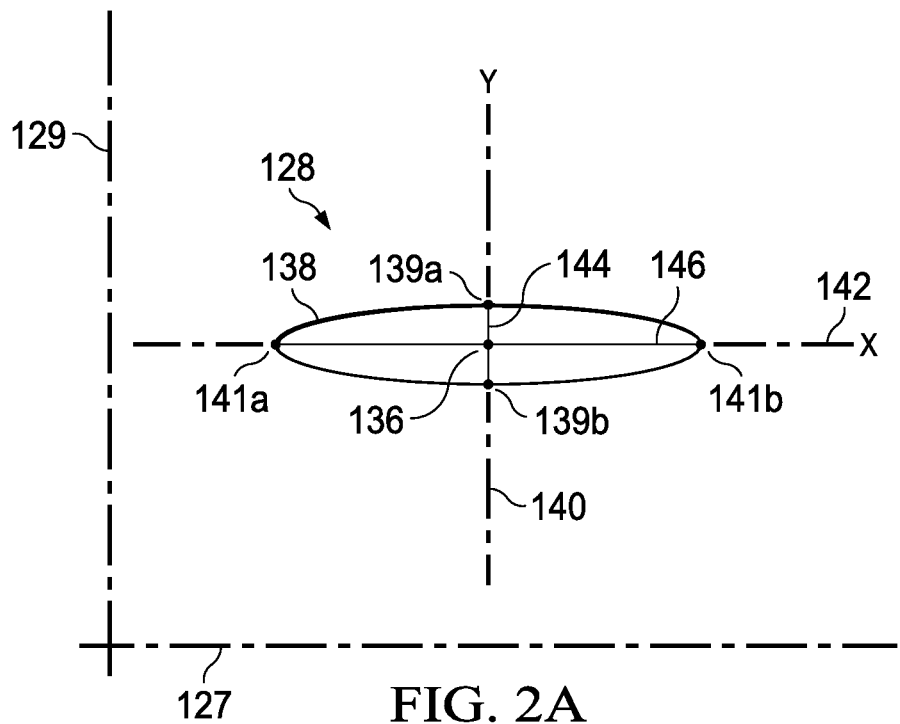
FIG. 2A is a schematic view, illustrating details that may be associated with some embodiments of a hole of the bolster of FIG. 1.
Figure 2B:
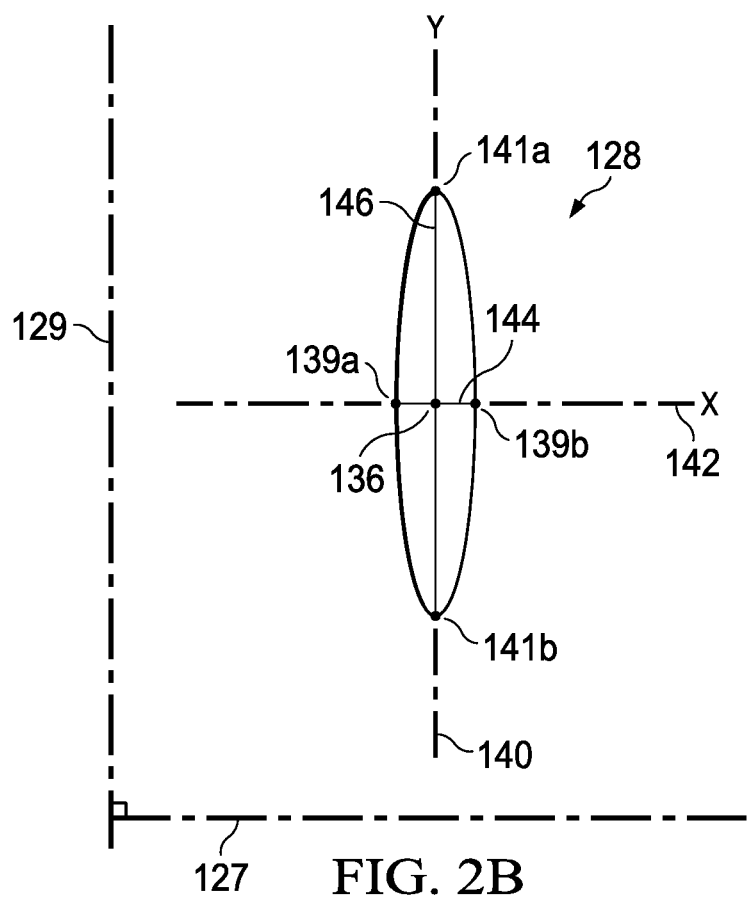
FIG. 2B is schematic view, illustrating details that may be associated with some alternative embodiments of a hole of the bolster of FIG. 1.

Referring more specifically to FIG. 2A, an example of one of the holes 128 having an elliptical shape is shown. Each of the holes 128 may include a center 136 and a perimeter 138. The holes 128 may have an average width to length ratio. For reference, each of the holes 128 may have an X-axis 142 extending through the center 136 between opposing vertices 141a and 141b of the ellipse and parallel to the first orientation line 127, and a Y-axis 140 extending through the center 136 between opposing co-vertices 139a and 139b of the ellipse and parallel to the second orientation line 129. The width to length ratio of each of the holes 128 may be defined as a ratio of a line segment 144 (width dimension) on the Y-axis 140 extending from co-vertex 139a to co-vertex 139b or from co-vertex 139b to co-vertex 139a, to a line segment 146 (length dimension) on the X-axis 142 extending from vertex 141a to vertex 141b or from vertex 141b to vertex 141a. If a length of the line segment 144 is 2.0 mm and the length of the line segment 146 is 4.0 mm, the width to length ratio would be 2.0/4.0 or about 0.5. In some embodiments, the holes 128 have an average width to length ratio of ≤about 0.75, ≤about 0.5, ≤about 0.25 or ≤about 0.10, preferably less than ≤about 0.50. In some embodiments, the holes 128 have an average width to length ratio of about 0.025 to about 0.75, about 0.05 to about 0.50 or about 0.25 to about 0.50. The holes 128 are not limited to the orientation as shown in FIG. 2A, but can be oriented in any suitable configuration as needed, preferably so long as the holes 128 have a width to length ratio as described above. For example, in other embodiments as illustrated in FIG. 2B, the hole 128 may be oriented such that the line segment 144 (width dimension) on the X-axis 142 is parallel to the first orientation line 127, and the line segment 146 (length dimension) on the Y-axis 140 is parallel to the second orientation line 129.

In some embodiments, an effective area of the holes 128 may be selected to permit flow of particulates through the holes 128. In some embodiments, an effective area of each of the holes 128 may be large enough to facilitate collapse of the hole, for example, in a direction perpendicular to the first orientation line 127, and generate a closing force 131, but not too large such that tissue is drawn into the bolster 114. In some embodiments, each of the holes 128 may have an effective width of about 2 mm. In some embodiments, each of the holes 128 may have an effective length of about 10 mm. The effective dimensions of the holes 128 should be distinguished from the porosity of the material forming the walls 130 of the bolster 114. Generally, an effective length or width of the holes 128 is an order of magnitude larger than the effective diameter of the pores of a material forming the bolster 114. For example, the effective width of the holes 128 may be larger than about 1 mm, while the walls 130 may be formed from foam having a pore size less than about 600 microns. In some embodiments, the pores of the walls 130 may not create openings that extend all the way through the material of the bolster 114.

Figure 3:
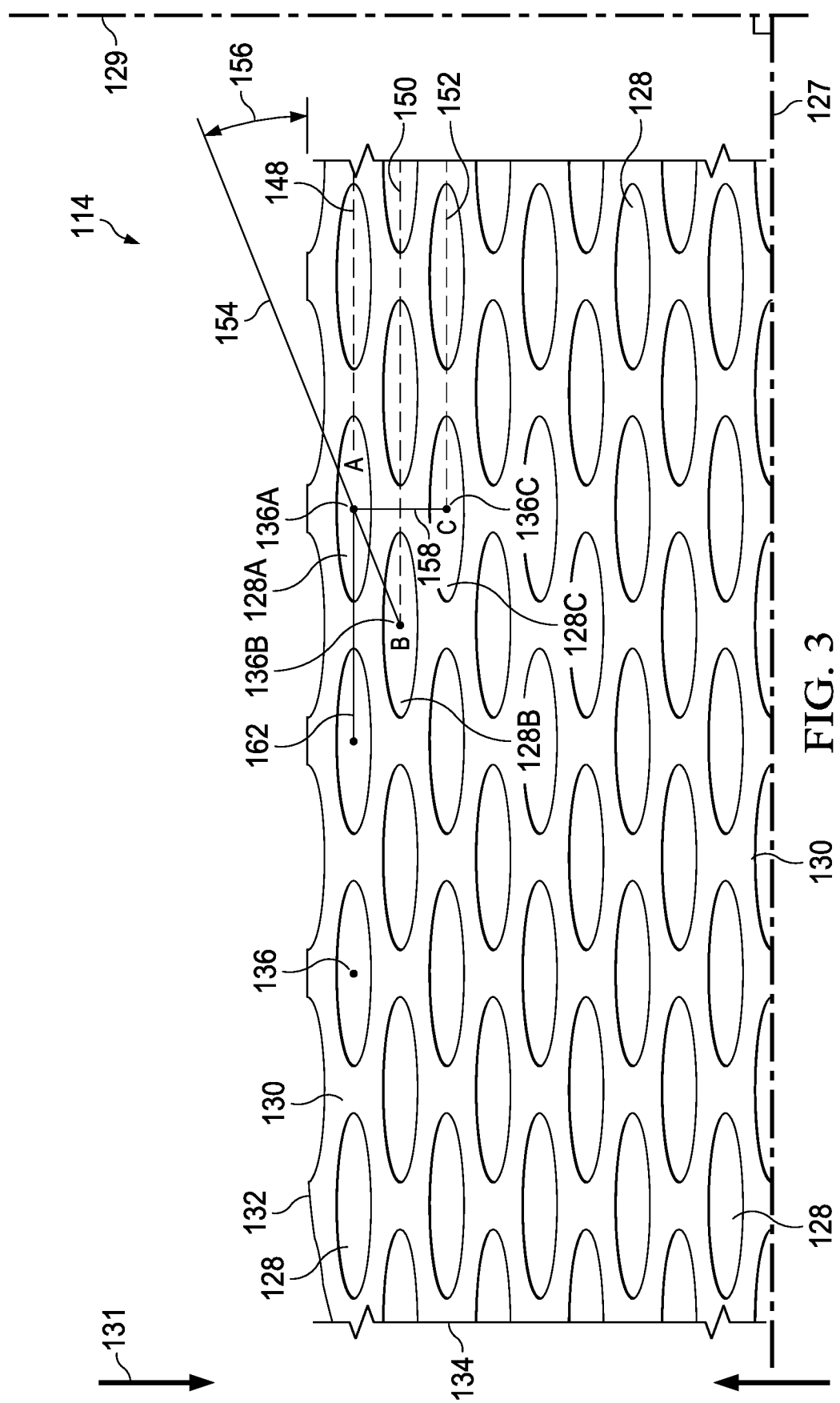
FIG. 3 is a plan view, illustrating details that may be associated with some alternative embodiments of the holes of the bolster of FIG. 1.

Referring to FIG. 3, a portion of another example of the bolster 114 is shown. The bolster 114 of FIG. 3 may include the first plurality of holes 128 aligned in a pattern of parallel rows, for example two or more parallel rows, to form an array. The pattern of parallel rows may include an array including a first row 148 of the holes 128, a second row 150 of the holes 128, and a third row 152 of the holes 128. In some embodiments, the centers 136 of the holes 128 in adjacent rows, for example, the first row 148 and the second row 150, may be characterized by being offset from the second orientation line 129 along the first orientation line 127. Alternatively, the centers 136 of the holes 128 in adjacent rows, for example, the first row 148 and the second row 150, may be characterized by being substantially aligned along the first orientation line. In some embodiments, a line connecting the centers of adjacent rows may form a strut angle with the first orientation line 127. For example, a first hole 128A in the first row 148 may have a center 136A, and a second hole 128B in the second row 150 may have a center 136B. A strut line 154 may connect the center 136A with the center 136B. The strut line 154 may form an angle 156 with the first orientation line 127. The angle 156 may be the strut angle of the bolster 114. In some embodiments, the strut angle may be less than about 90°. In other embodiments, the strut angle may be between about 30° and about 70° relative to the first orientation line 127. In other embodiments, the strut angle may be about 66° from the first orientation line 127. In some embodiments, for example, in a ball and strut configuration further described below, there may be four different strut angles including two angles of at least about 90° and two angles of less than or equal to about 90°. Generally, as the strut angle decreases, a stiffness of the bolster 114 in a direction parallel to the first orientation line 127 may increase. Increasing the stiffness of the bolster 114 parallel to the first orientation line 127 may increase the compressibility of the bolster 114 perpendicular to the first orientation line 127. Consequently, if negative pressure is applied to the bolster 114, the bolster 114 may be more compliant or compressible in a direction perpendicular to the first orientation line 127. By increasing the compressibility of the bolster 114 in a direction perpendicular to the first orientation line 127, the bolster 114 may collapse to apply a closing force, for example a closing force 131, to the opening 120 of the tissue site 102, as described in more detail below.

In some embodiments, the centers 136 of the holes 128 in adjacent rows, for example, the center 136A of the first hole 128A in the first row 148 and a center 136B of a hole 128B in the second row 150, may be spaced from each other parallel to the second orientation line 129 by a length 158.

In some embodiments, the length 158 may be greater than an effective diameter of the hole 128. If the centers 136 of holes 128 in adjacent rows are separated by the length 158, the walls 130 parallel to the first orientation line 127 may be considered continuous. Generally, the walls 130 may be continuous if the walls 130 do not have any discontinuities or breaks between holes 128. In some embodiments, the centers of the holes 128 in the same row, for example, the centers 136A of the first holes 128A in the first row 148, may be spaced from each other parallel to the first orientation line 127 by a width 162. In some embodiments, the width 162 may be less than, equal to, or greater than the length 158.

Regardless of the shape of the holes 128, the holes 128 in the bolster 114 may leave void spaces in the bolster 114 and on the surface of the bolster 114 so that only the walls 130 of the bolster 114 remain exposed. It may be desirable to minimize the walls 130 so that the holes 128 may collapse, causing the bolster 114 to collapse and generate a closing force 131 in a direction perpendicular to the first orientation line 127. However, it may also be desirable not to minimize the walls 130 so much that the bolster 114 becomes too fragile for sustaining the application of a negative pressure. The void space percentage of the holes 128 may be equal to the percentage of the volume or surface area of the void spaces created by the holes 128 to the total volume or surface area of the bolster 114. In some embodiments, the void space percentage may be between about 40% and about 60%. In other embodiments, the void space percentage may be about 55%.

In some embodiments, the holes 128 may be formed during molding of the bolster 114. In other embodiments, the holes 128 may be formed by cutting, melting, or vaporizing the bolster 114 after the bolster 114 is formed. For example, a through-hole may be formed by reaming, drilling, or milling a hole completely through the bolster 114. Additionally or alternatively, the holes 128 may be laser-cut into the bolster 114.

In some embodiments, formation of the holes 128 may thermoform the material of the bolster 114, causing the interior surface of the holes 128 to be non-porous. For example, laser-cutting the holes 128 into the bolster 114 may plastically deform the material of the bolster 114, closing any pores on the interior surfaces of the holes 128. Additionally or alternatively, a smooth interior surface of the holes 128 may be formed by a applying or coating a smooth material to the holes 128. In some embodiments, a smooth interior surface may limit or otherwise inhibit ingrowth of tissue into the bolster 114 through the holes 128.

Figure 4A:
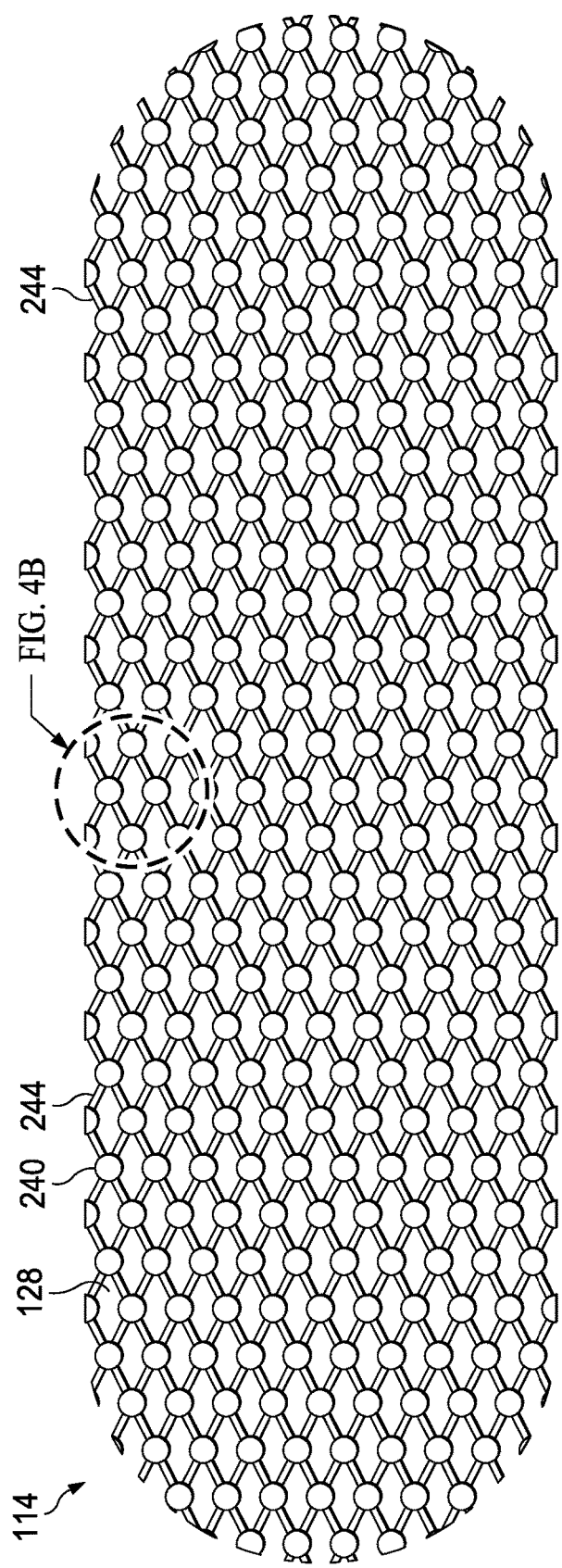
FIG. 4A is a plan view, illustrating details that may be associated with an alternative embodiment of a bolster.
Figure 4B:
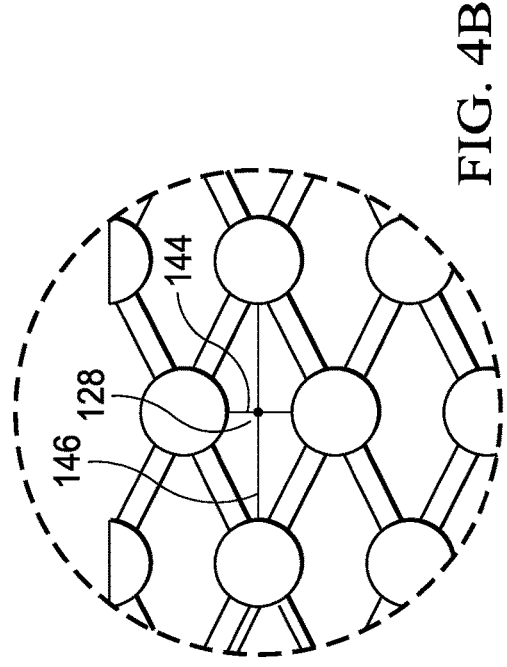
FIG. 4B is an exploded view of the bolster FIG. 4A, illustrating details of the bolster.

In other embodiments, the holes 128 may have other shapes and orientations, for example, preferably having a width to length ratio as discussed above. Examples of other suitable shapes and orientations for the holes 128 include, but are not limited to hexagonal, oval, rhombus, rhomboid, trapezoidal, rectangular, triangular, conical, or amorphous or irregular or a combination thereof. For example, FIG. 4A illustrates another example of the bolster 114 in which the holes 128 have diamond-shaped cross-sections. Additionally or alternatively, the bolster 114 may be formed of a ball and strut structure including a plurality of balls 240 and struts 244. As shown in FIG. 4B, each of the holes 128 may have a line segment 144 representing width and a line segment 146 representing length. In some embodiments, the holes 128 may have an average width to length ratio as described above, e.g., ≤about 0.5. In some embodiments, a bolster layer formed of a ball and strut structure may comprise a polymer and be formed via injection molding.

Figure 5A:
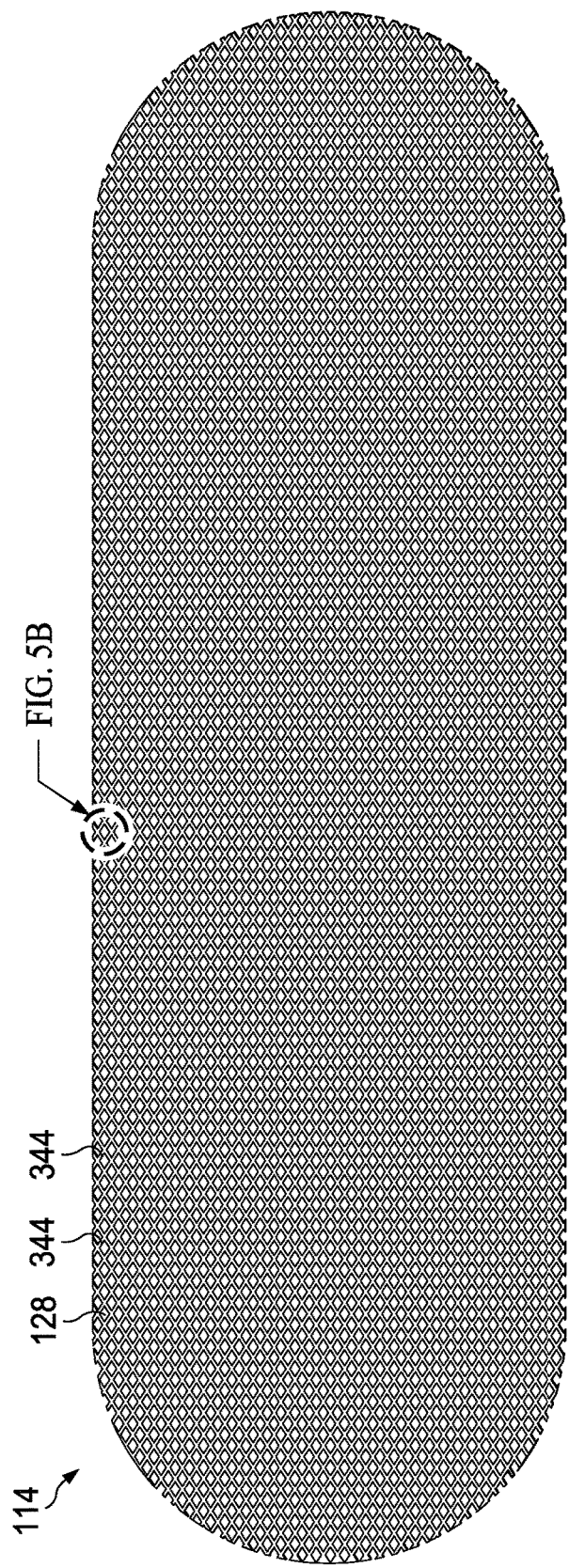
FIG. 5A is a plan view, illustrating details that may be associated with an alternative embodiment of a bolster.
Figure 5B:
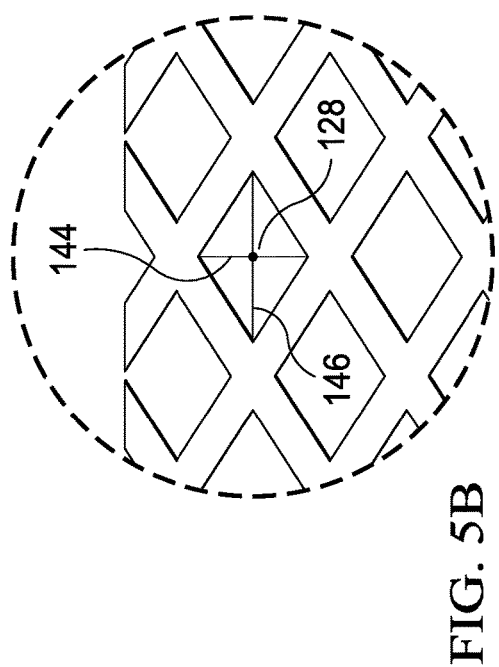
FIG. 5B is an exploded view of the bolster of FIG. 5A, illustrating details of the bolster.

FIG. 5A also illustrates another example of a bolster 114 including a plurality of diamond-shaped holes 128. The bolster 114 may be formed of a strut structure including a plurality of struts 344. As shown in FIG. 5B, each of the holes 128 may have a line segment 144 representing width and a line segment 146 representing length. In some embodiments, the holes 128 may have an average width to length ratio as described above, e.g., ≤about 0.5. In some embodiments, a bolster layer formed of a strut structure may comprise a polymer and be formed via extrusion techniques.

In some embodiments, the bolster 114 may be formed from a substantially hydrophilic material, a substantially hydrophobic material, or a combination thereof. As used herein, the term "hydrophilic" refers to a material, which has an affinity for water. That is, a hydrophilic substance or moiety tends to substantially attract water, can wick water, and/or is wetted by water. As used herein, the term "hydrophobic" refers to a material, which lacks an affinity for water. That is, a hydrophobic material tends to substantially repel water, is substantially insoluble in water, does not substantially mix with, wick, or be wetted by water or to do so only to a very limited degree and/or does not absorb water or, again, to do so only to a very limited degree. In some embodiments, the bolster 114 may be substantially porous (e.g., a porous foam) or substantially non-porous (e.g., non-porous, close-celled foam).

In some embodiments, the bolster 114 can comprise or be formed from any suitable material, for example, a material which can allow the transport of negative pressures to an opening on a tissue site and/or which can channel and/or wick wound fluid and/or wound debris away from the tissue site. For example, the bolster 114 can comprise or be formed from a material selected from the group consisting of a nonwoven material, a polymer and a combination thereof. In some embodiments, the bolster 114 may be formed from a nonwoven material. The nonwoven material may comprise natural fibers, synthetic fibers, continuous fibers, staple fibers, discontinuous fibers, bicomponent fibers and combinations thereof. In some embodiments, the nonwoven material may comprise polyolefin fibers (e.g., polypropylene, polyethylene), polyester, polyethylene terephthalate (PET), nylon, cotton, and combinations and copolymers thereof. A nonwoven material may be formed from various process known in the art, for example, meltblowing processes, spunbonding processes, spunlaid processes, airlaid processes, wetlaid processes, thermal bonded processes, bonded carded web processes, and combinations thereof. Examples of non-woven materials include, but are not limited to, co-polyester from Libeltex BVBA and HRM or polyolefin fibers in a matrix from Essentra.

In some embodiments, the bolster may be formed from a polymer, for example, a thermoplastic elastomer (TPE), silicone, or a foam. Examples of TPE include, but are not limited to styrene ethylene butylene styrene (SEBS) copolymers or thermoplastic polyurethane (TPU). The bolster 114 may be formed by combining sheets of TPE or TPU having a thickness between about 0.2 mm and about 2.0 mm to form a structure having the thickness 126. In some embodiments, the sheets of TPE or TPU may be bonded, welded, adhered, or otherwise coupled to one another. For example, in some embodiments, the sheets of TPE or TPU may be welded using radiant heat, radio-frequency welding, or laser welding. Supracor, Inc., Hexacor, Ltd., Hexcel Corp., and Econocorp, Inc. may produce suitable TPE or TPU sheets for the formation of the bolster 114. In some embodiments, the bolster 114 may be formed from a 3D textile, also referred to as a spacer fabric. Suitable 3D textiles may be produced by Heathcoat Fabrics, Ltd., Baltex, and Mueller Textil Group.

In some embodiments, the bolster 114 may be formed from foam. For example, cellular foam, open-cell foam, reticulated foam, or porous tissue collections, may be used to form the bolster 114. In some embodiments, the bolster 114 may be formed of grey foam or Zotefoam. Grey foam may be polyester polyurethane foam having about 60 pores per inch (ppi). Zotefoam may be a closed-cell, cross-linked polyolefin foam. In some non-limiting examples, the bolster 114 may comprise or consist essentially of be reticulated polyurethane foam such as found in GRANUFOAM™ dressing or V.A.C. VERAFLO™ dressing, both available from Kinetic Concepts, Inc. of San Antonio, Tex.

In some embodiments, the bolster 114 may comprise or consist essentially of foam that is mechanically or chemically compressed to increase the density of the foam at ambient pressure. Foam that is mechanically or chemically compressed may be referred to as compressed foam or felted foam. Compressed foam may be characterized by a firmness factor, which may be defined as a ratio of the density of foam in a compressed state to the density of the same foam in an uncompressed state. For example, a firmness factor of 5 may refer to compressed foam having a density that is five times greater than a density of the same foam in an uncompressed state. Mechanically or chemically compressing foam may also reduce a thickness of the foam at ambient pressure when compared to the same foam that has not been compressed. Reducing a thickness of foam by mechanical or chemical compression may increase a density of the foam, which may increase the firmness factor of the foam. Increasing the firmness factor of foam may increase a stiffness of the foam in a direction that is parallel to a thickness of the foam. For example, increasing a firmness factor of the bolster 114 may increase a stiffness of the bolster 114 in a direction that is parallel to the thickness 126 of the bolster 114. In some embodiments, the bolster 114 may have a density of about 0.03 grams per centimeter$^3$ (g/cm$^3$) in its uncompressed state. In its compressed state, the bolster 114 may have a firmness factor (FF) of about 5, and the density may be about 0.15 g/cm$^3$.

Generally, if compressed foam is subjected to negative pressure, the compressed foam exhibits less deformation or compression set than a similar uncompressed foam. If the bolster 114 is formed of compressed foam, the thickness 126 of the bolster 114 may deform less than if the bolster 114 is formed of a comparable uncompressed foam. The decrease in deformation may be caused by the increased stiffness as reflected by the firmness factor. If subjected to the stress of negative pressure, the bolster 114 formed of compressed foam may flatten less than the bolster 114 that is formed from uncompressed foam. Consequently, when negative pressure is applied to the bolster 114, the stiffness of the bolster 114 in the direction parallel to the thickness 126 of the bolster 114 can allow the bolster 114 to be more compliant or compressible in other directions, e.g., a direction parallel to the tissue surface 105 or in a direction perpendicular to the opening 120 of the tissue site 102. The pore size of a foam material may vary according to needs of the bolster 114 and the amount of compression of the foam. For example, in some embodiments, uncompressed foam may have pore sizes in a range of about 400 microns to about 600 microns. If the same foam is compressed, the pore sizes may be smaller than when the foam is in its uncompressed state.

In some embodiments, the bolster 114 may be formed from a polymer via injection molding or extrusion techniques.

Figure 6:
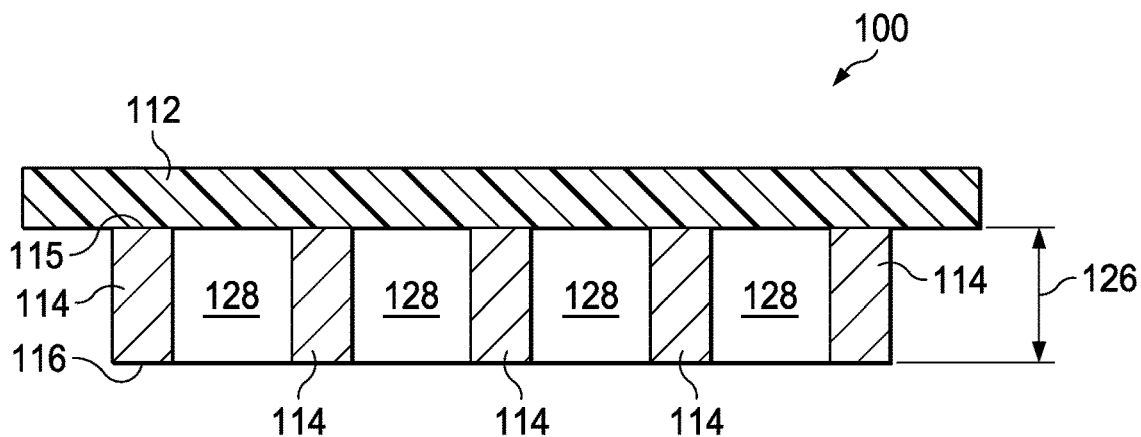
FIG. 6 is a cross-sectional view, illustrating details that may be associated with some embodiments of a dressing including a cover and a bolster.

FIG. 6 illustrates further details that may be associated with some embodiments of a dressing 100. In some embodiments, the dressing 100 can comprise a cover 112 and the bolster 114. The cover 112 may be adjacent to the first surface 115 of the bolster 114. In some embodiments, the cover 112 may provide a bacterial barrier and protection from physical trauma. The cover 112 may also be constructed from a material that can reduce evaporative losses and provide a fluid seal between two components or two environments, such as between a therapeutic environment and a local external environment. The cover 112 may be, for example, an elastomeric film or membrane that can provide a seal adequate to maintain a negative pressure at a tissue site for a given negative-pressure source. The cover 112 may have a high moisture-vapor transmission rate in some applications. For example, the MVTR may be at least 300 g/m$^2$ per twenty-four hours in some embodiments. In some example embodiments, the cover 112 may be a polymer drape, such as a polyurethane film, that is permeable to water vapor but impermeable to liquid. Such drapes typically have a thickness in the range of about 25 microns to about 50 microns. For permeable materials, the permeability generally should be low enough that a desired negative pressure may be maintained.

Figure 7:
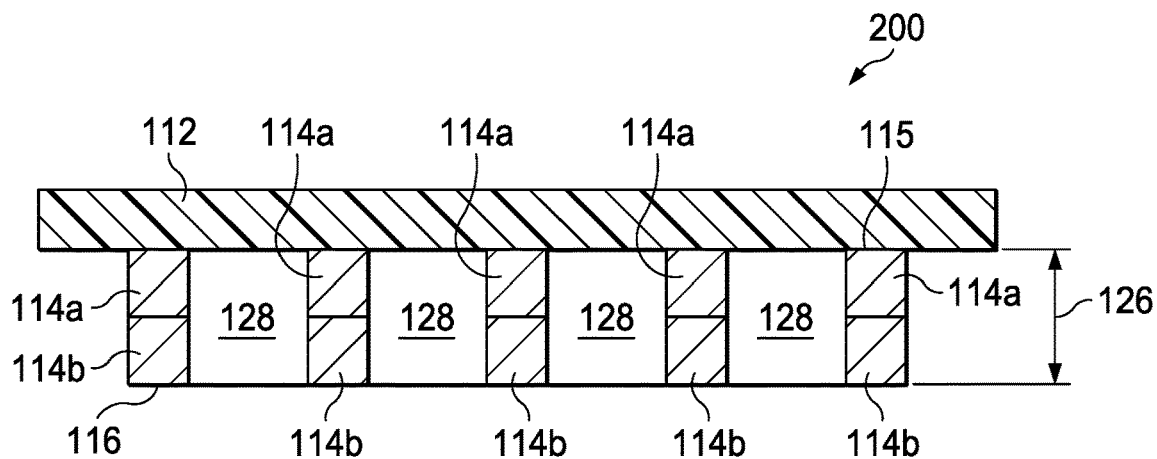
FIG. 7 is a cross-sectional view, illustrating details that may be associated with some embodiments of a dressing including a cover, and a multilayered bolster.

In some embodiments, the bolster 114 may be a single layer, for example as shown in FIG. 6. Alternatively, the bolster 114 may be multilayered; for example, the bolster may comprise two or more layers, three or more layers, four or more layers, etc. For example, as shown in FIG. 7 in a dressing 200, the bolster 114 may comprise two or more layers, such as first bolster 114a and a second bolster 114b.

Figure 8A:
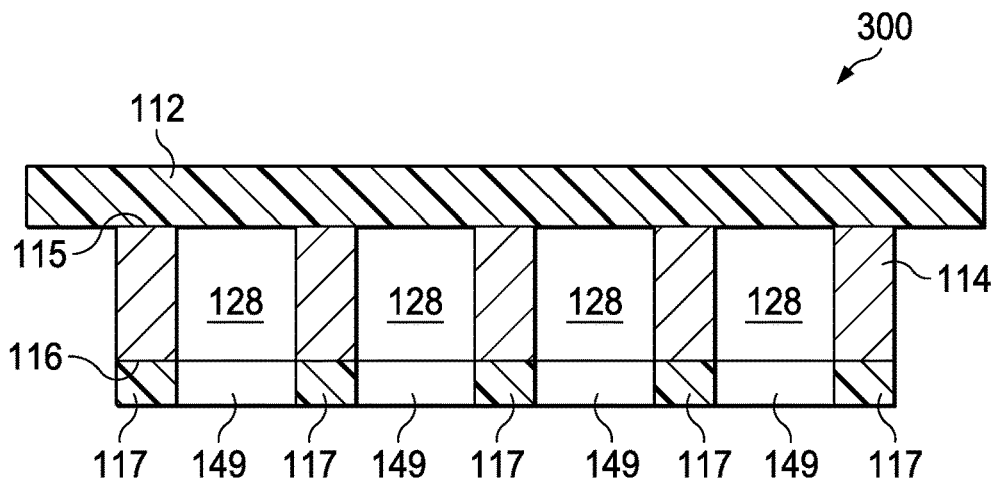
FIG. 8A is a cross-sectional view, illustrating details that may be associated with some embodiments of a dressing including a cover, a bolster, and a protective layer.
Figure 8B:
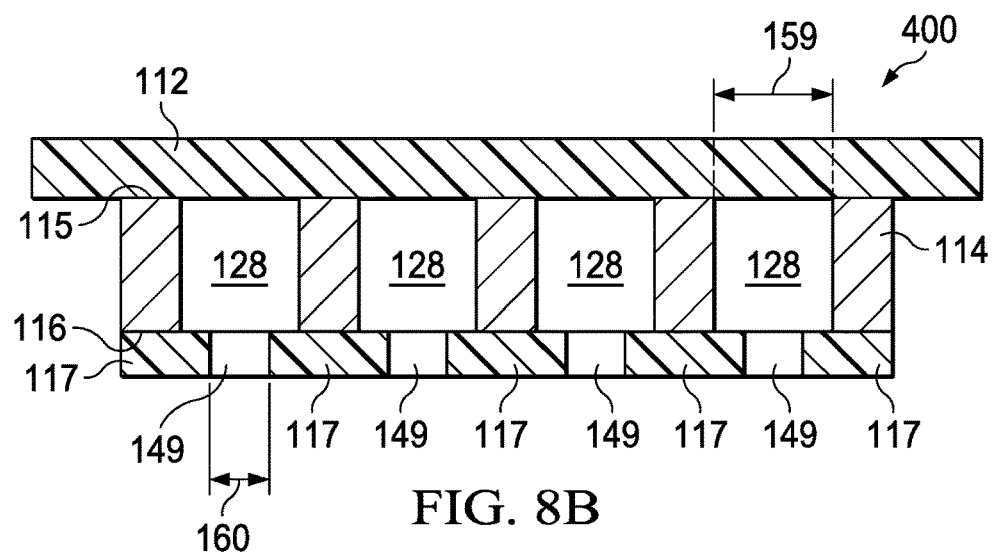
FIG. 8B is a cross-sectional view, illustrating details that may be associated with some alternative embodiments of a dressing including a cover, a bolster, and a protective layer.

In some embodiments, a dressing may further include a protective layer generally adjacent to a second surface of the bolster and adapted to be adjacent to an opening on a tissue site. For example, as illustrated in FIG. 8A, a protective layer 117 may be adjacent to the second surface 116 of the bolster 114 in a dressing 300. The protective layer 117 may comprise a second plurality of holes, for example a second plurality of holes 149, which may extend through at least portion of the protective layer 117. The second plurality of holes 149 may be substantially adjacent to the first plurality of holes 128. Generally, the second plurality of holes 149 may have substantially similar dimensions as the first plurality of holes 128 and/or the second plurality of holes 149 may have dimensions smaller than the dimensions of the first plurality of holes 128. For example, the second plurality of holes 149 may have substantially the same average width, average length and/or average diameter as the first plurality of holes 128, as shown in FIG. 8A. In some embodiments, the second plurality of holes 149 may have an average width, an average length and/or an average diameter less than or equal to an average width, an average length and/or an average diameter of the first plurality of holes 128. As illustrated in FIG. 8B, a second plurality of holes 149 in a protective layer 117 has a width 160 of the hole 149 less than a width 159 of the hole 128 in a dressing 400.

The holes 149 may have any suitable shape or configuration. Examples of shapes and orientations for the holes 149 include, but are not limited to slit, slot, hexagonal, elliptical, oval, rhombus, rhomboid, trapezoidal, rectangular, triangular, conical, or amorphous or irregular or a combination thereof. In some embodiments, the shape of the holes 149 may be the same or different than the shape of the holes 128. In some embodiments, an average width to length ratio of the holes 149 may be as described above for the holes 128. In some embodiments, an average width to length ratio of the holes 149 may be the same or different than an average width to length ratio of the holes 128.

In some embodiments, the protective layer 117 may be coextensive with the bolster 114, for example, the protecting layer 117 may cover substantially the entire second surface 116 of the bolster 114. In other embodiments, the protective layer 117 may be larger or smaller than the bolster 114. In some embodiments, the protective layer 117 may have a thickness that is less than the thickness 126 of the bolster 114. In some embodiments, the protective layer 117 may be a protective mesh, a film, a woven material or a non-woven material. In some embodiments, the protective layer 117 may be laminated to the bolster 114. In some embodiments, the protective layer 117 may inhibit irritation of the tissue site 102. In some embodiments, when the bolster 114 is formed from a foam material, the protecting layer 117 can be present in the dressing.

Figure 9:
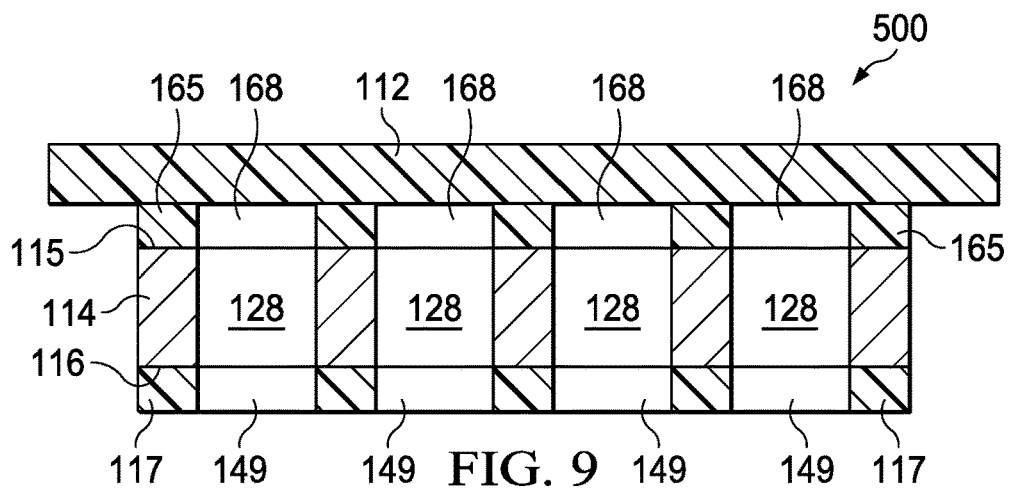
FIG. 9 is a cross-sectional view, illustrating details that may be associated with some embodiments of a dressing including a cover, a top layer, a bolster, and a protective layer.

In some embodiments, a dressing may further include a top layer generally adjacent to first surface of the bolster and adjacent to a cover. For example, as illustrated in FIG. 9, a top layer 165 may be adjacent to the first surface 115 of the bolster 114 and the cover 112 in a dressing 500. In some embodiments, the top layer 165 may be coextensive with the bolster 114. In other embodiments, the top layer 165 may be larger or smaller than the bolster 114. In some embodiments, the top layer 165 may have a thickness that is less than the thickness 126 of the bolster 114. In some embodiments, the top layer 165 may be a protective mesh, a film, a perforated film, a woven material or a non-woven material. In some embodiments, the top layer 165 may be laminated to the bolster 114.

In some embodiments, the top layer 165 may comprise a third plurality of holes, for example a third plurality of holes 168, which may extend through at least portion of the top layer 165. The third plurality of holes 168 may be substantially adjacent to the first plurality of holes 128. Generally, the third plurality of holes 168 may have substantially similar dimensions as the first plurality of holes 128 and/or the third plurality of holes 168 may have dimensions smaller than the dimensions of the first plurality of holes 128. For example, the third plurality of holes 168 may have substantially the same average width, average length and/or average diameter as the first plurality of holes 128, as shown in FIG. 9. In some embodiments, the third plurality of holes 168 may have an average width, an average length and/or an average diameter greater than, less than or equal to an average width, an average length and/or an average diameter of the first plurality of holes 128.

The holes 168 may have any suitable shape or configuration. Examples of shapes and orientations for the holes 168 include, but are not limited to slit, slot, hexagonal, elliptical, oval, rhombus, rhomboid, trapezoidal, rectangular, triangular, conical, or amorphous or irregular or a combination thereof. In some embodiments, the shape of the holes 168 may be the same or different than the shape of the holes 128. In some embodiments, an average width to length ratio of the holes 168 may be as described above for the holes 128. In some embodiments, an average width to length ratio of the holes 168 may be the same or different than an average width to length ratio of the holes 128.

Figure 10:
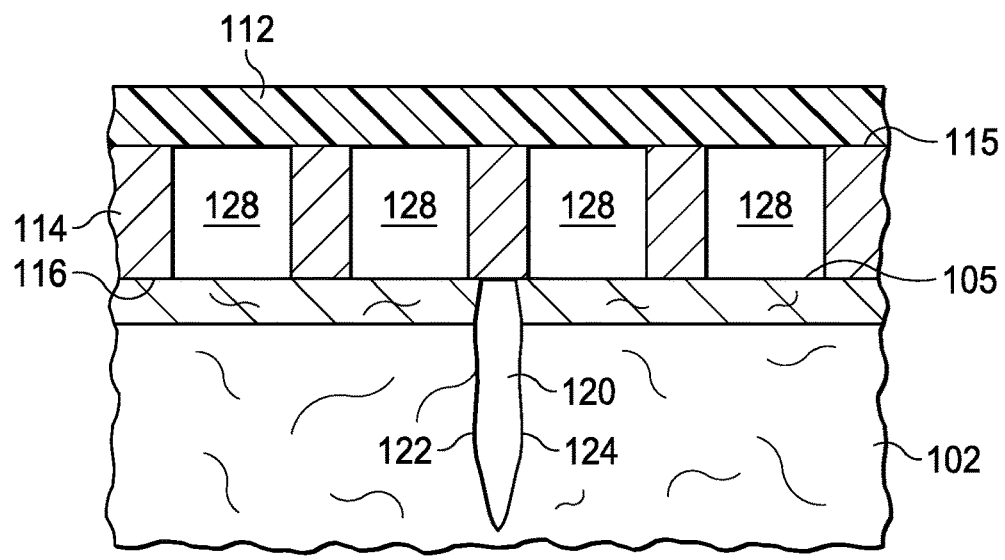
FIG. 10 is a cross-sectional view, illustrating details that may be associated with some embodiments of the dressing of FIG. 1 positioned on a tissue site.

In use, as shown in FIG. 10, the bolster 114 can be placed on a tissue site 102, and the second surface 116 of the bolster 114 may be adjacent to the tissue site 102. The tissue site 102 may have a tissue surface 105 and an opening 120, for example, a linear wound, through the tissue surface 105 along a length of the tissue site 102. The tissue site 102 may also have a first wall 122 and a second wall 124 extending from the opening 120 in the tissue surface 105 generally parallel to each other along the length and depth of the tissue site 102. The bolster 114 may cover the opening 120 in the tissue surface 105 of the tissue site 102. Although not shown in FIG. 10, the protective layer 117 may be positioned between the second surface 116 of the bolster 114 and the tissue surface 105 surrounding the opening 120.

Generally, in operation, the first orientation line 127 and the second orientation line 129 may be lines used to orient the bolster 114 relative to the tissue site 102. In some embodiments, the first orientation line 127 and the second orientation line 129 may be used to refer to desired directions of contraction for the bolster 114. For example, if the first orientation line 127 is oriented parallel to the opening 120, the desired direction of contraction may be parallel to the second orientation line 129 and perpendicular to the first orientation line 127. Generally, the bolster 114 may be placed at the tissue site 102 so that the first orientation line 127 is parallel to the opening 120 and may cover portions of the tissue surface 105 on both sides of the opening 120. In some embodiments, the first orientation line 127 may be coincident with the opening 120.

II. System

Figure 11B:
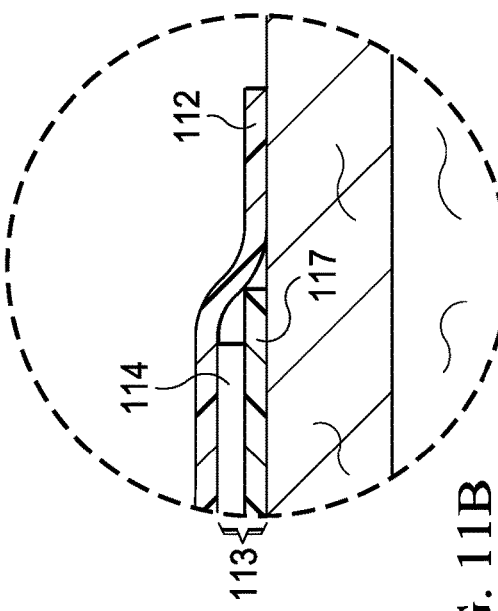
FIG. 11B is an exploded view of the system of FIG. 11A, illustrating details of the dressing including a cover and a tissue interface.
Figure 11A:
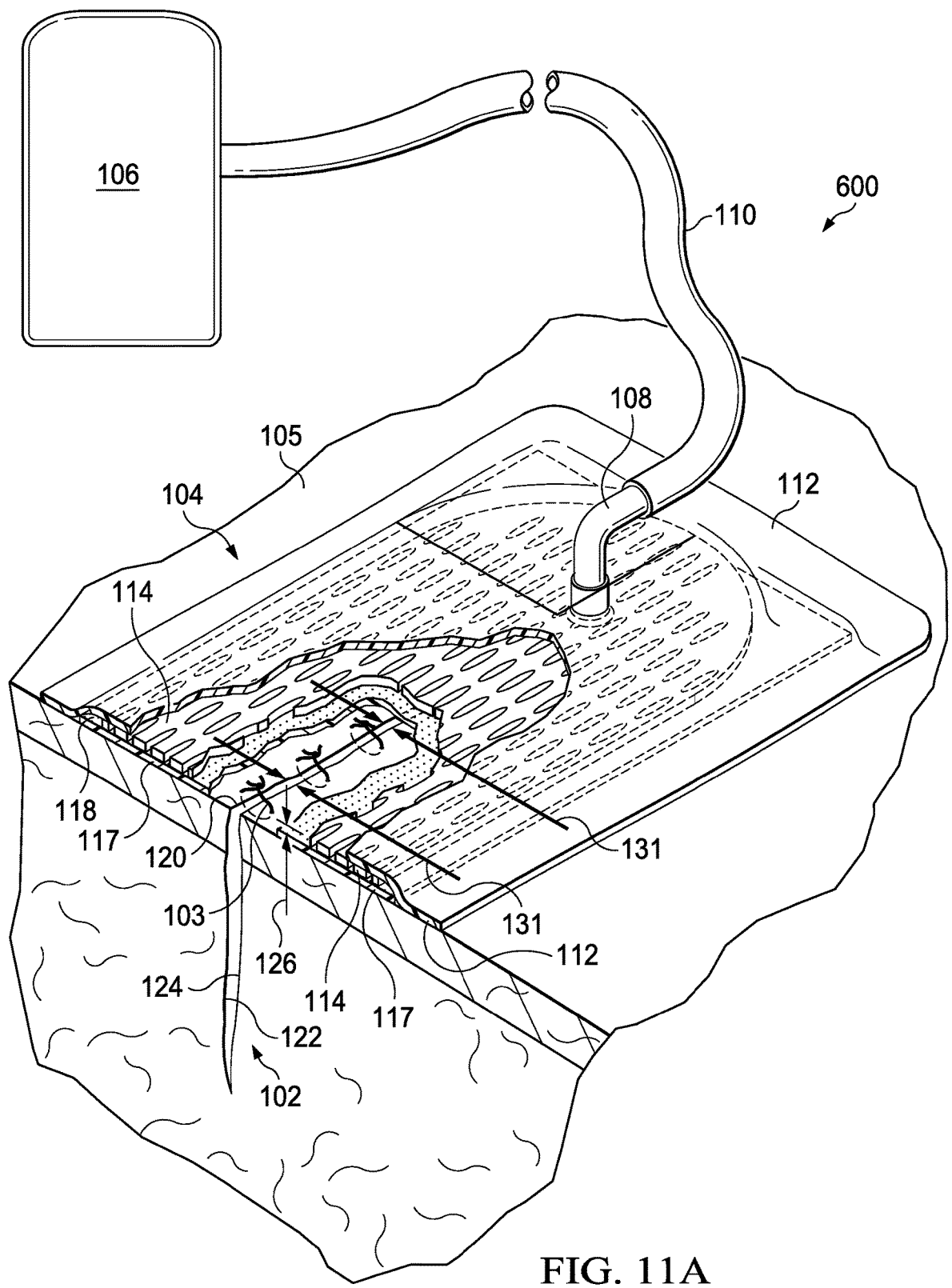
FIG. 11A is a cut-away view with a portion shown in elevation, illustrating details that may be associated with some embodiments of a system.

A system for closing an opening through a surface of a tissue site is also described herein. For example, FIG. 11A illustrates details that may be associated with some embodiments of a system 100 that can be applied to the tissue site 102. The system 100 may include a dressing and a negative-pressure source adapted to be fluidly coupled to the dressing. For example, a dressing 104 may be fluidly coupled to a negative-pressure source 106, as illustrated in FIG. 11A. A dressing may be fluidly coupled to a negative-pressure source by a connector and a tube. The dressing 104, for example, may be fluidly coupled to the negative-pressure source 106 by a connector 108 and a tube 110. A dressing may generally include a cover and a tissue interface. As illustrated in FIG. 11B, the dressing 104, for example, may include the cover 112 and a tissue interface 113. In some embodiments, the tissue interface 113 may comprise or consist essentially of one or more bolsters, such as the bolster 114. The tissue interface 113 may additionally include a protective layer, such as the protective layer 117.

In general, components of the system 100 may be coupled directly or indirectly. For example, the negative-pressure source 106 may be directly coupled to the dressing 104 and indirectly coupled to the tissue site 102 through the dressing 104. Components may be fluidly coupled to each other to provide a path for transferring fluids (i.e., liquid and/or gas) between the components.

In some embodiments, components may be fluidly coupled through a tube, such as the tube 110. A "tube," as used herein, broadly refers to a tube, pipe, hose, conduit, or other structure with one or more lumina adapted to convey a fluid between two ends. Typically, a tube is an elongated, cylindrical structure with some flexibility, but the geometry and rigidity may vary. In some embodiments, components may additionally or alternatively be coupled by virtue of physical proximity, being integral to a single structure, or being formed from the same piece of material. Coupling may also include mechanical, thermal, electrical, or chemical coupling (such as a chemical bond) in some contexts.

A mechanical means may be used to apply a closing force to a tissue site. A mechanical means of closing a tissue site may include sutures, staples, hooks, and other devices configured to apply a closing force. For example, one or more stitches 103 may be used to close the opening 120. Generally, sutures, staples, and other devices may be configured to apply a closing force to a surface of a tissue site or to other tissue peripheral to the tissue site. For example, a thread may be inserted into punctures and drawn across an opening of an incision. The thread may be held under tension with a knot or other securing mechanism to draw opposing sides of an opening together. Sutures and staples may apply a localized stress to tissue near the punctures where the sutures penetrate tissue. The stitches 103 may be surgical sutures, for example, which may be used to hold tissue together following an injury or a surgical procedure. Generally, stitches may be thread formed from absorbable material such as polyglycolic acid, polylactic acid, monocryls, and polydioxanone, or non-absorbable materials such as nylon, polyester, polyvinylidene fluoride, and polypropylene. The stitches 103 may apply a closing force to the opening 120 by being placed under tension to draw the first wall 122 and the second wall 124 toward each other.

In operation, a tissue interface, such as the tissue interface 113, may be placed within, over, on, or otherwise proximate to the tissue site 102. A cover may be placed over a tissue interface and sealed to tissue near a tissue site. For example, the tissue interface 113 may be placed over the stitches 103 and the tissue site 102, and the cover 112 may be sealed to undamaged epidermis peripheral to the tissue site 102. Thus, the cover 112 can provide a sealed therapeutic environment 118 proximate to the tissue site 102 that is substantially isolated from the external environment, and the negative-pressure source 106 can reduce the pressure in the sealed therapeutic environment 118.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically refers to a position in a fluid path relatively closer to a negative-pressure source. Conversely, the term "upstream" refers to a position relatively further away from a negative-pressure source. Similarly, it may be convenient to describe certain features in terms of fluid "inlet" or "outlet" in such a frame of reference. This orientation is generally presumed for purposes of describing various features and components of negative-pressure therapy systems herein. However, the fluid path may also be reversed in some applications (such as by substituting a positive-pressure source for a negative-pressure source) and this descriptive convention should not be construed as a limiting convention.

"Negative pressure" generally refers to a pressure less than a local ambient pressure. A local ambient pressure may be a pressure in a local environment external to the sealed therapeutic environment 118 provided by the dressing 104. In many cases, a local ambient pressure may also be the atmospheric pressure at which a tissue site is located. Alternatively, negative pressure may be a pressure that is less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure.

A negative-pressure source, such as the negative-pressure source 106, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure source may be housed within or used in conjunction with other components, such as sensors, processing units, alarm indicators, memory, databases, software, display devices, or user interfaces that further facilitate negative-pressure therapy. While the amount and nature of negative pressure applied to a tissue site may vary according to therapeutic requirements, the pressure is generally a low vacuum, also referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

A tissue interface, such as the bolster tissue interface 113, can generally be adapted to contact a tissue site. A tissue interface may be partially or fully in contact with a tissue site. If a tissue site is a wound, for example, a tissue interface may partially or completely fill the wound, or may be placed over the wound. A tissue interface may take many forms, and may have many sizes, shapes, or thicknesses depending on a variety of factors, such as the type of treatment being implemented or the nature and size of a tissue site. For example, the size and shape of a tissue interface may be adapted to the contours of deep and irregular shaped tissue sites.

In some embodiments, the tissue interface 113 may be a manifold or may include a manifold. For example, the bolster 114 may function as a manifold. A "manifold" in this context generally includes any substance or structure providing a plurality of pathways adapted to collect or distribute fluid across a tissue site under negative pressure. For example, a manifold may be adapted to receive negative pressure from a source and distribute the negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways of a manifold may be channels interconnected to improve distribution or collection of fluids across a tissue site. For example, cellular foam, open-cell foam, reticulated foam, porous tissue collections, and other porous material such as gauze or felted mat generally include pores, edges, and/or walls adapted to form interconnected fluid pathways. Liquids, gels, and other foams may also include or be cured to include apertures and flow channels. In some illustrative embodiments, a manifold may be a porous foam material having interconnected cells or pores adapted to uniformly (or quasi-uniformly) distribute negative pressure to a tissue site.

In an example in which a tissue interface may be made from a hydrophilic material, the tissue interface may also wick fluid away from a tissue site, while continuing to distribute negative pressure to the tissue site. The wicking properties of a tissue interface may draw fluid away from a tissue site by capillary flow or other wicking mechanisms. An example of hydrophilic foam that may be suitable is a polyvinyl alcohol, open-cell foam such as found in V.A.C. WHITEFOAM™ dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

A tissue interface may further promote granulation at a tissue site when pressure within the sealed therapeutic environment is reduced. For example, any or all of the surfaces of a tissue interface may have an uneven, coarse, or jagged profile that can induce microstrains and stresses at a tissue site if negative pressure is applied through a tissue interface. A tissue interface may further serve as a scaffold for new cell-growth, or a scaffold material may be used in conjunction with the tissue interface to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

An attachment device may be used to attach the cover 112 to an attachment surface, such as undamaged epidermis, a gasket, or another cover. In some embodiments, an attachment surface may be tissue surrounding a tissue site, such as the tissue surface 105 surrounding the opening 120. An attachment device may take many forms. For example, an attachment device may be a medically-acceptable, pressure-sensitive adhesive that extends about a periphery, a portion, or an entire sealing member. In some embodiments, for example, some or all of the cover 112 may be coated with an acrylic adhesive having a coating weight between about 25 grams per square meter (gsm) and about 65 gsm. Thicker adhesives or combinations of adhesives may be applied in some embodiments to improve the seal and reduce leaks. Other example embodiments of an attachment device may include a double-sided tape, paste, hydrocolloid, hydrogel, silicone gel, or organogel.

A linear tissue site or linear wound, such as an incision, may often be created during a surgical procedure if a surgeon or other clinician uses a cutting instrument, such as a scalpel, to pierce and cut through at least a portion of a tissue site. Following a surgical procedure, a closing force may be applied to an opening of an incision to facilitate healing. A closing force may be a force that is substantially parallel to the tissue surface 105 and urges the first wall 122 and the second wall 124 toward each other to close the opening 120. Closure of an opening may help maintain a healing environment for internal structures of a tissue site, as well as inhibit entry of bacteria or other harmful substances into the tissue site.

III. Methods of Use

Methods of using the wound dressings and systems as described herein are provided for treating a tissue site on a patient. In some embodiments, the method may comprise positioning a dressing as described herein adjacent to a tissue site. In some embodiments, the tissue site comprises an opening, such as a linear wound. In some embodiments, the linear wound may be present on the abdomen or knee of the patient. In other embodiments, the tissue site may comprise a cavity, and positioning the dressing may comprise positioning at least a portion of the dressing inside the cavity.

The dressing may comprise a bolster as described herein, for example, the bolster 114 may comprise the first surface 115, the second surface 116, and the first plurality holes 128 extending through at least a portion of the bolster 114. In some embodiments, the bolster may be single layer or may be multilayered, for example, comprising two or more layers. In some embodiments, the bolster may have thickness as described herein, for example ≤about 6.0 mm or a thickness of about 1.0 mm to about 6.0 mm. In some embodiments, positioning the dressing may comprise positioning the second surface of the bolster adjacent to and/or covering the tissue site. In some embodiments, the first plurality of holes may have an average width to length ratio as described herein, for example, ≤about 0.5 or about 0.05 to about 0.5. In some embodiments, at least a portion of the first plurality of holes may extend through the bolster, for example as a through-hole from the first surface to the second surface of the bolster. In other embodiments, at least a portion of the first plurality of holes may be a blind hole and have a depth that is less than the thickness of the bolster.

In some embodiments, the dressing may further comprise a protective layer as described herein, for example, protective layer 117, wherein the protective layer may be adjacent to the second surface of the bolster and adjacent to the tissue site. In some embodiments, the protective layer may comprise a second plurality of holes, for example, holes 139, wherein the second plurality of holes are substantially adjacent to the first plurality of holes. In some embodiments, the dressing may further comprise a top layer as described herein, for example, top layer 165, adjacent to the first surface of the bolster.

In some embodiments, the method may generally comprise collapsing the bolster parallel to the surface of the tissue site to generate a closing force on the tissue site. In some embodiments, the method may further comprise positioning a sealing member, for example, a cover, over the dressing. Additionally, the method may further comprise sealing the cover to the tissue site, for example, to tissue surrounding the tissue site, to form a sealed space enclosing the wound dressing. A negative pressure source as described herein may be fluidly coupled to the sealed space. In some embodiments, collapsing the bolster may comprise supplying negative pressure to the sealed space with the negative pressure source. Additionally or alternatively, collapsing the bolster may comprise supplying negative pressure to the bolster with the negative pressure source Referring now to both FIGS. 1 and 3, the holes 128 may form a pattern depending on the geometry of the holes 128 and the alignment of the holes 128 between adjacent and alternating rows in the bolster 114 with respect to the first orientation line 127. If the bolster 114 is subjected to negative pressure, the holes 128 of the bolster 114 may collapse. In some embodiments, the average width to length ratio (e.g. ≤about 0.5) of the holes 128, may cause the bolster 114 to collapse along the second orientation line 129 perpendicular to the first orientation line 127 as shown in more detail in FIG. 12. Additionally or alternatively, void space percentage and the strut angle may also cause the bolster 114 to collapse along the second orientation line 129 perpendicular to the first orientation line 127. If the bolster 114 is positioned on the tissue surface 105 of the tissue site 102 so that the first orientation line 127 coincides with the opening 120, the bolster 114 may generate the closing force 131 along the second orientation line 129 such that the tissue surface 105 is contracted in the same direction to facilitate closure of the opening 120 and draw the first wall 122 to the second wall 124 as shown in more detail in FIG. 12. In other words, the bolster 114 may be positioned on the tissue surface 105 of the tissue site 102 so that length of the holes 128 in the bolster 114 may be in direction substantially parallel to the length of the tissue site 102. The closing force 131 may be optimized by adjusting the factors described above. In some embodiments, the closing force 131 may be about 4 N.

Figure 12:
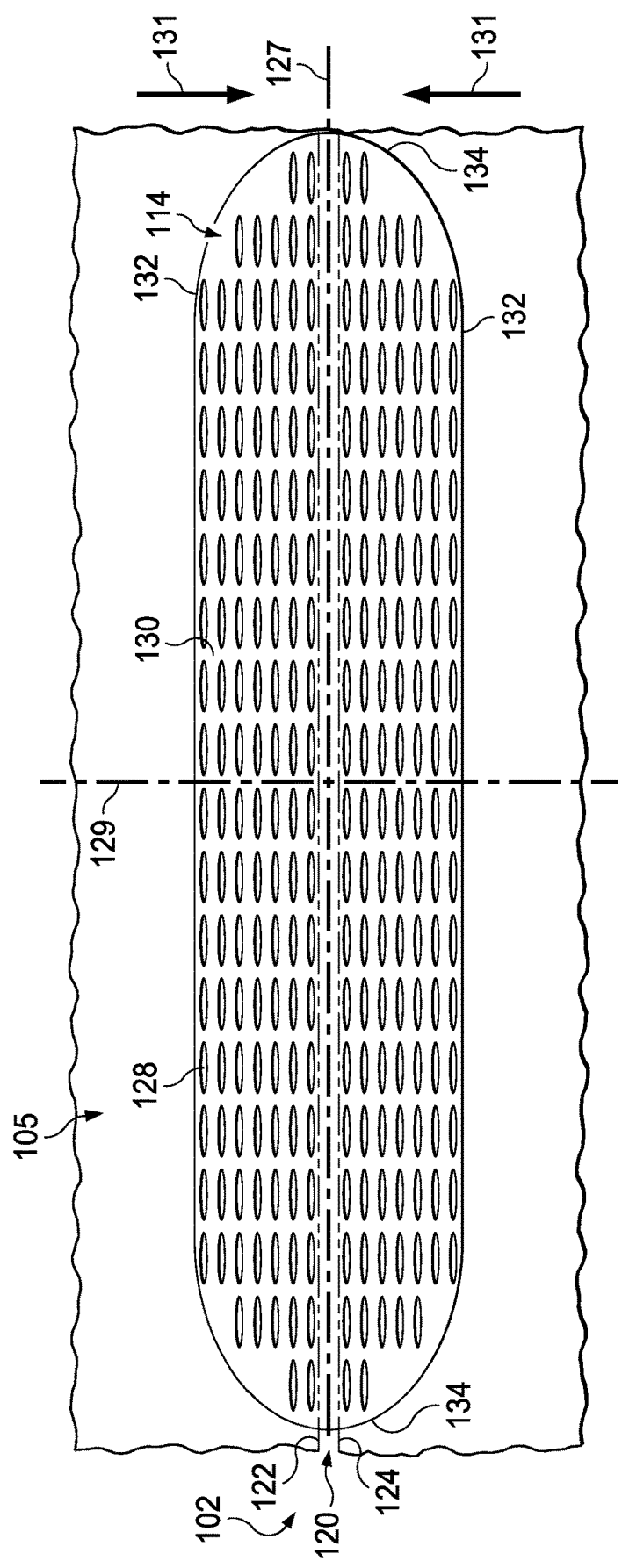
FIG. 12 is a plan view, illustrating details that may be associated with some embodiments of the bolster of FIG. 1 in a second position.
Figure 13:
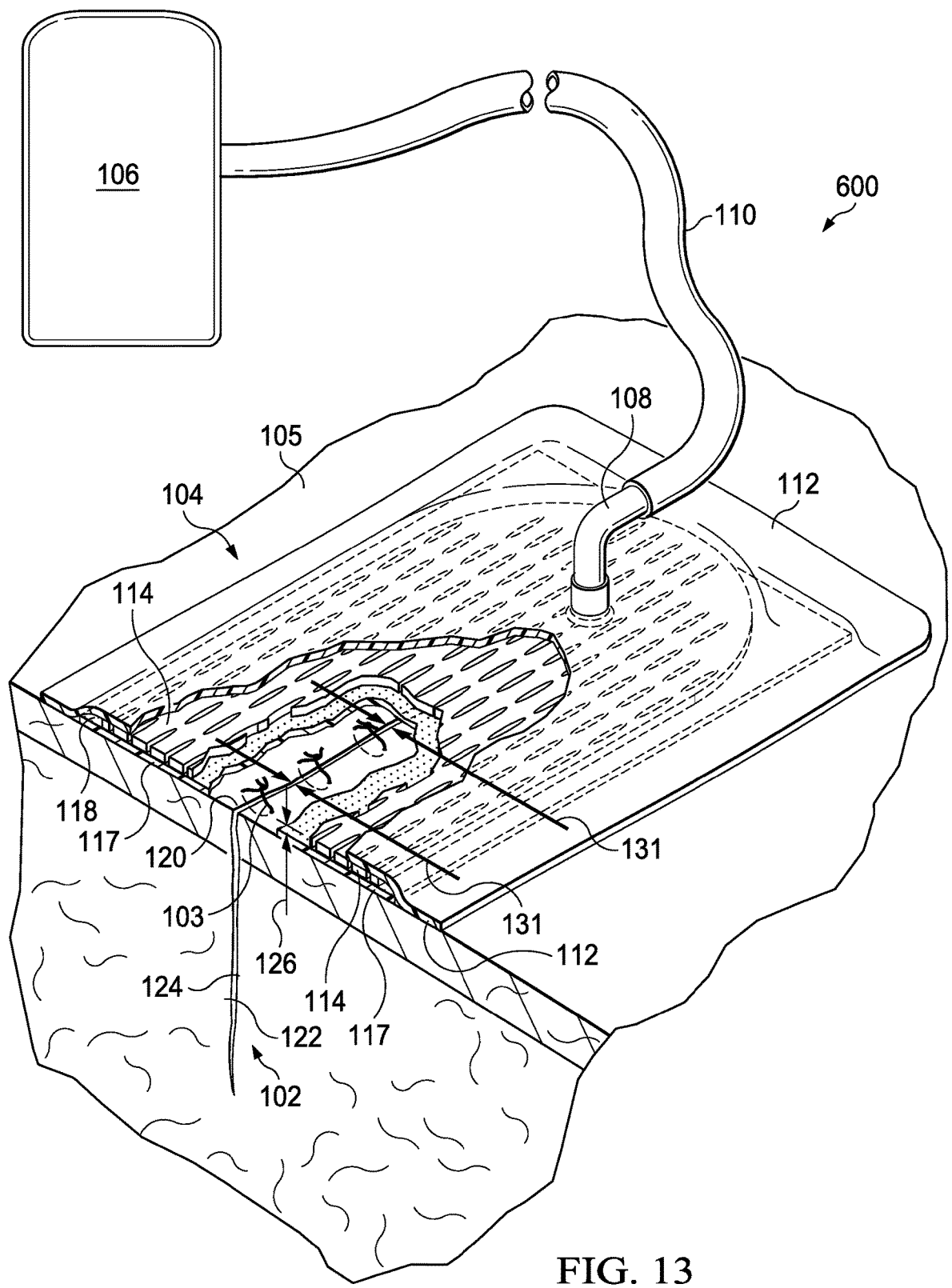
FIG. 13 is a cut-away view with a portion shown in elevation, illustrating details that may be associated with some embodiments of the system of FIG. 11.
Figure 14:
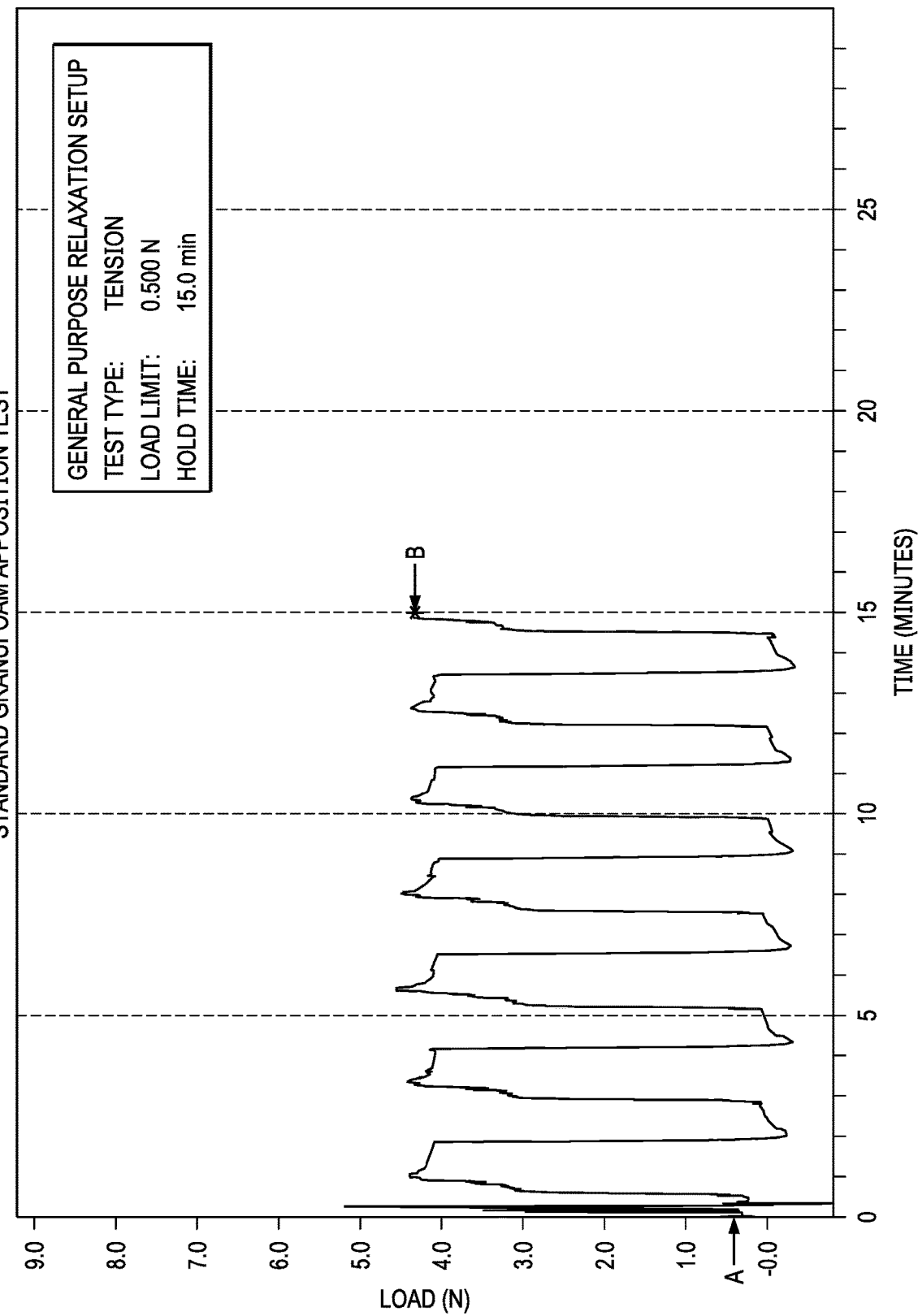
FIG. 14 illustrates results of apposition testing of GranuFoam® bolster without holes.

FIG. 13 is a cut-away view of an example of the system 100, illustrating additional details that may be associated with some embodiments. As illustrated in FIG. 13, the bolster 114 is in the second position, or contracted position, as shown in FIG. 12. In operation, negative pressure may be supplied to the sealed therapeutic environment 118 with the negative-pressure source 106. In response to the supply of negative pressure, the bolster 114 may collapse from the position illustrated in FIG. 11 to the position illustrated in FIG. 13, drawing edges of the bolster 114 toward a center of the bolster 114 in response to collapse of the holes 128. In some embodiments, the thickness 126 of the bolster 114 may remain substantially the same. In other embodiments, the bolster 114 may compress and the thickness 126 of the bolster 114 may decrease. Thus, in some embodiments, the bolster 114 may experience a closing force 131 and a compressing force, which compresses thickness 126. In some embodiments, negative pressure may be supplied to the sealed therapeutic environment 118 until a pressure in the sealed therapeutic environment 118 is about a therapy pressure. In some embodiments, the sealed therapeutic environment 118 may remain at the therapy pressure for a therapy period. In some embodiments, the therapy period may be a time period that allows for opposing sides of the opening 120 to heal. In some embodiments, the therapy period may be cyclic, having a period in which negative pressure may be applied to the tissue site 102 and a period in which negative pressure may be vented from the tissue site 102. In other embodiments, the therapy period may be longer or as shorter as needed to supply appropriate negative-pressure therapy to the tissue site 102.

If the bolster 114 is in the second position of FIG. 13, the bolster 114 may exert the closing force 131 parallel to the tissue surface 105 of the tissue site 102 toward the opening 120. The closing force 131 may urge the first wall 122 and the second wall 124 toward one another. In some embodiments, the closing force 131 may close the opening 120. The closing force 131 may also relieve localized stresses that may be caused by the stitches 103, reducing the risk of additional trauma to the tissue site 102.

IV. Kit

In some embodiments, a bolster, such as the bolster 114, having a first surface, a second surface and a first plurality of holes extending through at least a portion of the bolster, such as holes 128, may be provided as a component of a wound dressing kit. In some embodiments, the bolster may have a thickness as described herein, such as thickness 126, for example, ≤about 6.0 mm. In some embodiments, the holes may have a width to length ratio as described herein, for example, ≤about 0.5. The kit can provide a user, such as a clinician, the ability to customize the bolster to a particular tissue site.

In some embodiments, the kit may optionally comprise a cover, such as the cover 112. The cover may be separate from the bolster or adjacent to the first surface of the bolster. In some embodiments, the kit may optionally comprise a protective layer, such as protective layer 117, having a second plurality of holes extending through at least a portion of the protective layer, such as holes 149. The protective layer may be separate from the bolster or adjacent to the second surface of the bolster. In some embodiments, if the protective layer is present adjacent to the second surface of the bolster, the second plurality of holes may be substantially adjacent to the first plurality of holes. In some embodiments, the second plurality of holes may have substantially the same average width, average length and/or average diameter as the first plurality of holes. In some embodiments, the second plurality of holes may have an average width, an average length and/or an average diameter less than or equal to an average width, an average length and/or an average diameter of the first plurality of holes.

In some embodiments, the kit may optionally comprise a top layer, such as top layer 165. The top layer may be separate from the bolster or present between the cover and the bolster, for example, adjacent to the first surface of the bolster.

The systems, apparatuses, methods and kits described herein may provide significant advantages. For example, the system 100 can provide a closing force to facilitate closure of a tissue site. In some embodiments, the system 100 may include a dressing that can be placed over other mechanical closure devices, such as stitches, to provide and distribute a closing force generally perpendicular to a linear tissue site, such as an incision. In some embodiments, the system 100 may apply a closing force that urges opposing sides of an opening in a linear tissue site toward each other, thereby at least partially relieving localized stresses that may be caused by punctures and stitches.

The bolster 114 can facilitate the transmission or production of significant closing forces or apposition forces for closing a wound upon the application of negative pressure. The closing forces generated by the described bolsters meet or exceed other bolsters designed for a similar purpose. In combination with the described holes, the described bolster may have a low profile, for example, a thickness ≤6.0 mm, resulting in the bolster having a lower volume. The described bolsters with a lower volume can better conform to curved surfaces, such as a knee or abdomen, when incorporated into a dressing. Furthermore, the described lower volume bolsters when used in conjunction with a therapy device, such a negative pressure therapy system, can improve the therapy device's duty cycle and efficiency and thus, its battery life may increase. Additionally, the described bolsters may not suffer the effects of compression set, which can reduce a lateral closing force of the bolster. The described bolsters may also assist in closure of an incisional tissue site by distributed force along a length of the incisional opening, reducing potential trauma that may be caused by point loading such as with sutures, staples or hooks.

While shown in a few illustrative embodiments, a person having ordinary skill in the art will recognized that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

EXAMPLES

Example 1—Apposition Testing

Apposition testing was performed on bolster samples with and without a plurality of holes. The bolster samples tested are shown in Table 1 below.

TABLE 1

Bolster Samples

| Bolster Material | Bolster Thickness | Holes (Yes or No) | Hole Shape | Hole Dimensions (width; length) | Hole Width to Length Ratio |
|---|---|---|---|---|---|
| GRANUFOAM ™ | 18 mm | No | — | — | — |
| Essentra* with holes | 6 mm | Yes | Diamond | 2 mm; 10 mm | 0.2 |
| Essentra without holes | 6 mm | No | — | — | — |
| Silicone polymeric ball and strut | 6 mm | Yes | Diamond | 2 mm; 10 mm | 0.2 |

*Formed from compressed HRM polyolefin fibers in a matrix

A silicone wound model with a linear wound was used for the apposition testing. The wound model was comprised of various densities of silicone overlaid onto one another to replicate human epidermal skin layer with its associated subcutaneous fat layer and muscle layer. The silicone wound model used included three layers of silicone as follows: a first layer (simulated skin layer) about 1 mm to 2 mm thick with a Shore 00 hardness of about 35; a second adjacent layer (simulated fat layer) about 5 mm to 10 mm thick with a Shore 00 hardness of about 5; and a third adjacent layer (simulated muscle layer) about 30 mm to 40 mm thick with a Shore 00 hardness of about 45.

For the apposition testing, each of the bolster samples were applied over the linear wound in the silicone wound model with a SENSAT.R.A.C.™ dressing, which was connected to a therapy unit. The Lloyd, a calibrated material tensometer, applied a fixed force as a preload (~0.5 N) which resulted in a given displacement and then measured the force applied to the wound model when negative pressure was applied to the dressing. The negative pressure (about −125 mm Hg) application was applied for 1 minute, then released for 1 minute, then reapplied for another minute, then released again for a couple cycles (for example, at least three cycles). The negative pressure can be applied from a therapy unit, such as an InfoVAC™ Therapy Unit or V.A.C.ULTA™ Therapy Unit. The results showing load (N) versus time (minutes) for the GRANUFOAM™ bolster, the Essentra with holes bolster, the Essentra without holes bolster, and the silicone polymeric ball and strut bolster are shown in FIGS. 14, 15, 16 and 17, respectively.

What is claimed is:

1. A dressing for closing an opening through a surface of a tissue site, the dressing comprising:
a cover adapted to form a sealed space over the opening;
a bolster having a first surface and a second surface and adapted to be positioned adjacent to the opening, wherein the bolster comprises a first layer defining the first surface, a second layer defining the second surface, the first layer coupled to the second layer, and a first plurality of holes extending through at least a portion of the first layer and the second layer of the bolster, wherein the first plurality of holes have an average width to length ratio less than or equal to 0.50; and
a top layer adjacent to the first surface of the bolster, the top layer comprising a third plurality of holes extending through at least a portion of the top layer, the third plurality of holes substantially adjacent to the first plurality of holes.

2. The dressing of claim 1, wherein the bolster has a thickness less than or equal to 6.0 mm.

3. The dressing of claim 1, wherein the bolster has a thickness of about 1.0 mm to 6.0 mm.

4. The dressing of claim 1, wherein the bolster is hydrophilic or hydrophobic.

5. The dressing of claim 1, wherein at least a portion of the bolster is porous or non-porous.

6. The dressing of claim 1, wherein the bolster comprises a material selected from the group consisting of a nonwoven material and a polymer.

7. The dressing of claim 6, wherein the polymer is a foam.

8. The dressing of claim 7, wherein the foam is a compressed foam.

9. The dressing of claim 1, wherein the first plurality of holes have an average width to length ratio of 0.05 to 0.50.

10. The dressing of claim 1, wherein at least a portion of the first plurality of holes have a depth less than a thickness of the bolster.

11. The dressing of claim 1, wherein each of the holes of the first plurality of holes have a shape selected from a group consisting of hexagonal, elliptical, oval, rhombus, rhomboid, trapezoidal, rectangular, triangular, conical and a combination thereof.

12. The dressing of claim 1, wherein the first plurality of holes are present in an array.

13. The dressing of claim 12, wherein the array comprises two or more parallel rows.

14. The dressing of claim 1, further comprising a protective layer adjacent to the second surface of the bolster and adapted to be adjacent to the opening, wherein the protective layer comprises a second plurality of holes extending through at least a portion of the protective layer, wherein the second plurality of holes are substantially adjacent to the first plurality of holes.

15. The dressing of claim 14, wherein the second plurality of holes have an average effective diameter less than or equal to an average effective diameter of the first plurality of holes.

16. The dressing of claim 14, wherein each of the holes of the second plurality of holes have a shape selected from a group consisting of a slit, a slot, hexagonal, elliptical, oval, rhombus, rhomboid, trapezoidal, rectangular, triangular, conical and a combination thereof.

17. The dressing of claim 16, wherein the shape of each of the holes of the second plurality of holes is the same or different than a shape of each of the holes of the first plurality of holes.

18. The dressing of claim 14, wherein the protective layer comprises a material selected from the group consisting of a mesh, a film, a woven material, and a non-woven material.

19. The dressing of claim 1, wherein the dressing is configured to close the opening of a linear wound.

20. The dressing of claim 19, wherein the dressing is configured to close the opening of the linear wound on an abdomen of a patient.

21. A system for closing an opening through a surface of a tissue site, the system comprising:
the dressing of claim 1; and
a negative-pressure source adapted to be fluidly coupled to the dressing.

22. A dressing kit comprising:
a bolster comprising a first surface, a second surface, a first layer defining the first surface, a second layer defining the second surface, the first layer coupled to the second layer, and a first plurality of holes extending through at least a portion of the first layer and the second layer, wherein the holes have an average width to length ratio less than or equal to 0.50 and the bolster has a thickness of less than or equal to 6.0 mm;
a cover, wherein the cover is separate from the bolster or adjacent to the first surface of the bolster;
a protective layer comprising a second plurality of holes extending through at least a portion of the protective layer, wherein the protective layer is separate from the bolster or adjacent to the second surface of the bolster and the second plurality of holes are substantially adjacent to the first plurality of holes; and
a top layer, wherein the top layer is separate from the bolster or adjacent to the first surface of the bolster, the top layer comprising a third plurality of holes extending through at least a portion of the top layer, the third plurality of holes substantially adjacent to the first plurality of holes.

23. A dressing for closing an opening through a surface of a tissue site, the dressing comprising:
a cover adapted to form a sealed space over the opening;
a bolster having a first surface and a second surface and adapted to be positioned adjacent to the opening, wherein the bolster comprises a first layer defining the first surface, a second layer defining the second surface, the first layer coupled to the second layer, and a first plurality of holes extending through at least a portion of the first layer and the second layer, wherein the holes have an average width to length ratio 0.050 to 0.50, the bolster has a thickness of 1.0 mm to 6.0 mm, and the bolster comprises a non-woven material or a compressed foam; and
a top layer adjacent to the first surface of the bolster, the top layer comprising a third plurality of holes extending through at least a portion of the top layer, the third plurality of holes substantially adjacent to the first plurality of holes.

* * * * *